US009745257B2

(12) United States Patent
Lorenzano Menna et al.

(10) Patent No.: US 9,745,257 B2
(45) Date of Patent: Aug. 29, 2017

(54) PHENYL-GUANIDINE DERIVATIVES

(71) Applicants: Universidad Nacional de Quilmes, Buenos Aires (AR); Chemo Research, S.L., Madrid (ES)

(72) Inventors: Pablo Lorenzano Menna, Buenos Aires (AR); Daniel Fernando Alonso, Buenos Aires (AR); Daniel Eduardo Gómez, Buenos Aires (AR); Julieta Comin, Buenos Aires (AR)

(73) Assignees: UNIVERSIDAD NACIONAL DE QUILMES, Buenos Aires (AR); CHEMO RESEARCH, S.L., Madrid (ES)

( * ) Notice: Subject to any disclaimer, the term of this patent is extended or adjusted under 35 U.S.C. 154(b) by 369 days.

(21) Appl. No.: 14/348,577

(22) PCT Filed: Oct. 10, 2012

(86) PCT No.: PCT/EP2012/070004
§ 371 (c)(1),
(2) Date: Mar. 28, 2014

(87) PCT Pub. No.: WO2013/053726
PCT Pub. Date: Apr. 18, 2013

(65) Prior Publication Data
US 2014/0228388 A1 Aug. 14, 2014

Related U.S. Application Data

(60) Provisional application No. 61/545,804, filed on Oct. 11, 2011.

(51) Int. Cl.
| | |
|---|---|
| A61K 31/505 | (2006.01) |
| A61K 31/155 | (2006.01) |
| C07D 239/42 | (2006.01) |
| C07C 277/08 | (2006.01) |
| C07C 279/18 | (2006.01) |
| C07D 213/75 | (2006.01) |
| C07D 333/36 | (2006.01) |
| C07D 233/88 | (2006.01) |
| C07D 235/30 | (2006.01) |
| C07D 263/48 | (2006.01) |
| C07D 207/14 | (2006.01) |
| C07D 277/48 | (2006.01) |
| C07D 307/66 | (2006.01) |

(52) U.S. Cl.
CPC .......... *C07C 279/18* (2013.01); *A61K 31/155* (2013.01); *A61K 31/505* (2013.01); *C07C 277/08* (2013.01); *C07D 207/14* (2013.01); *C07D 213/75* (2013.01); *C07D 233/88* (2013.01); *C07D 235/30* (2013.01); *C07D 239/42* (2013.01); *C07D 263/48* (2013.01); *C07D 277/48* (2013.01); *C07D 307/66* (2013.01); *C07D 333/36* (2013.01)

(58) Field of Classification Search
None
See application file for complete search history.

(56) References Cited

U.S. PATENT DOCUMENTS

| | | | |
|---|---|---|---|
| 5,847,006 A | 12/1998 | Magar et al. | |
| 6,242,198 B1 * | 6/2001 | McBurney | A61K 31/155 424/427 |

FOREIGN PATENT DOCUMENTS

WO  WO 2010111713 A2 * 9/2010  ........... C07K 14/473

OTHER PUBLICATIONS

International Search Report and Written Opinion for PCT/EP2012/070004, mailed Mar. 22, 2012, 11 pgs.
Feng-Qi He et al., "Synthesis, Structure and Biological Activities of Some Novel N—(4,6-Disubstituted-pyrimidin-2-yl)-N'—(trifluoromethylphenyl)—guanidine Derivatrives," Chinese Journal of Chemistry, vol. 26., No. 8, Aug. 1, 2008, pp. 1481-1485.
Stefan Sperl et al., "(4-Aminomethyl)phenylguanidine derivatives as nonpeptidic highly selective inhibitors of human urokinase," Proceedings of the National Academy of Sciences, May 9, 2000, vol. 97, No. 10, pp. 5113-5118.
HongBin Wang et al., "Chimaerins, Novel Non-protein Kinase C Phorbol Ester Receptors, Associate with Tmp21-I (p. 23)," The Journal of Biological Chemistry, Feb. 8, 2002, vol. 277, No. 6, pp. 4541-4550.

* cited by examiner

*Primary Examiner* — Jeffrey S Lundgren
*Assistant Examiner* — Michael Schmitt
(74) *Attorney, Agent, or Firm* — Squire Patton Boggs (US) LLP

(57) ABSTRACT

Provided herein are phenyl-guanidine derivatives for the inhibition of Rac1 which blocks its interaction with guanosine exchange factors (GEFs) belonging to the DBL family as agents for the treatment of aggressive and/or resistant tumors, as well as pharmaceutical compositions comprising them, their use in therapy and processes for their preparation.

17 Claims, 9 Drawing Sheets

PHENYL-GUANIDINE DERIVATIVES

CROSS-REFERENCE TO RELATED APPLICATIONS

This application is a National Stage Application under Rule 1.371 of International Application No. PCT/EP2012/070004 filed Oct. 10, 2012 which claims the benefit of U.S. Provisional Patent Application Ser. No. 61/545,804 filed on Oct. 11, 2011, which are incorporated herein by reference.

The present invention relates to new series of phenyl-guanidine derivatives for the inhibition of Rac1 which blocks its interaction with guanosine exchange factors (GEFs) belonging to the DBL family as agents for the treatment of aggressive and/or resistant tumours, as well as to processes for their preparation, to pharmaceutical compositions comprising them and to their use in therapy.

BACKGROUND ART

Rho family GTPase are molecular switches that control signaling pathways regulating actin cytoskeleton reorganization, gene expression, cell cycle progression, cell survival, and other cellular processes. Among other functions, they participate in cell cycle and cell division regulation, being also involved in secretion, endocytosis, phagocytosis, membrane traffic and apoptosis.

Rho family proteins constitute one of three major branches of the Ras superfamily. Rho proteins share approximately 30 percent amino acid identity with the Ras proteins. At least 23 mammalian Rho family proteins have been identified thus far, including RhoA, Rac1 and Cdc42.

Tumor cells, besides presenting proliferation deregulation, they present alterations in their morphological characteristics and, in the case of metastasis, and they get the ability to pass through tissue barriers. Rho GTPases play an important role in controlling cell morphology and motility.

The obtaining of compounds capable of specifically inhibiting Rho-GTPases activity offers a specific alternative in cancer therapy.

The synthesis and herbicidal activity of some guanidine derivatives are described in Chinese Journal of Chemistry, 2008, vol. 26(8), pp. 1481-1485.

SUMMARY OF THE INVENTION

The present invention provides compounds that are potent and selective inhibitors of Rho GTPase cell proteins. Specifically, these compounds can be used to inhibit Rho-related Rac1 GTPase cell protein. Accordingly, these inhibitors can be used to treat diseases mediated by mammalian Rac1 cell proteins, i.e. they can be useful for the treatment of any condition mediated by Rho GTPase cell proteins, particularly by Rac1 cell proteins.

Therefore, a first aspect of the present invention relates to a compound of formula (I)

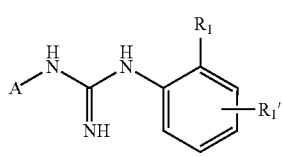
(I)

or a salt thereof, or any of its stereoisomeric forms or a mixture thereof wherein:

$R_1$ and $R_1'$ are independently selected from the group consisting of H, $(C_1-C_4)$alkyl, $CF_3$, F, Cl, Br, I, —CN, OH, $NH_2$, —$OCH_3$, and $NO_2$; with the proviso that at least one of $R_1$ and $R_1'$ are other than H;

A is a radical selected from linear or branched $(C_1-C_6)$ alkyl or one of the known carbocyclic or heterocyclic ring systems with 1-2 rings, wherein each of the rings forming the ring system
  has 5-7 members, each member independently selected from C, N, O, S, CH, $CH_2$, NH;
  is saturated, partially unsaturated or aromatic;
  being A substituted by one or more radical selected from the group consisting of H, halogen, nitro, cyano, linear or branched $(C_1-C_6)$alkyl, halo-$(C_1-C_6)$alkyl, linear or branched $(C_2-C_6)$alkenyl, —$OR_2$, —$COR_2$, —$COOR_2$, —$OC(O)R_2$, —$C(O)NR_3R_4$, —$NR_3R_4$, —$R_5NHR_6$, —$SR_2$, —$SO$—$R_2$, —$SO_2$—$R_2$, and —$SO_2NR_3R_4$;
  wherein
    each $R_2$ independently represents H or linear or branched $(C_1-C_4)$alkyl,
    each $R_3$ independently represents H or linear or branched $(C_1-C_4)$alkyl,
    each $R_4$ independently represents H, linear or branched $(C_1-C_6)$alkyl, phenyl, pyridine or quinoline; wherein the phenyl, pyridine and quinoline ring system is substituted by one or more radical selected from H, linear or branched $(C_1-C_4)$alkyl, and $NH_2$;
    $R_5$ and $R_6$ are independently selected from H, linear or branched $(C_1-C_4)$alkyl,
for use in the treatment of a condition mediated by Rho GTPase cell proteins, particularly by Rac1 cell proteins.

This first aspect may be formulated as a method of treating a condition mediated by Rho GTPase cell proteins, particularly Rac1, in a subject in need thereof, especially a human being, which comprises administering to the subject a compound of formula I or a pharmaceutically acceptable salt thereof together with pharmaceutical excipients or carriers.

Alternatively, this first aspect may be formulated as the use of a compound of formula I or a pharmaceutically acceptable salt thereof for the preparation of a medicament for the treatment of a condition mediated by Rho-GTPase cell proteins, particularly Rac1.

More preferably, the condition mediated by Rac1 is an aggressive and/or resistant tumour.

Another aspect of the invention relates to a pharmaceutical composition which comprises at least one compound of formula I or a pharmaceutically acceptable salt thereof and one or more pharmaceutically acceptable excipients or carriers.

Preferably, the pharmaceutical composition is an antitumoral pharmaceutical composition.

Another aspect provides a new compound of formula II

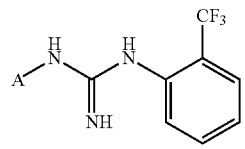
(II)

or a salt thereof, or any of its stereoisomeric forms or a mixture thereof wherein:

A is a radical of one of the known carbocyclic or heterocyclic ring systems with 1-2 rings,
  wherein each of the rings forming the ring system
    has 5-7 members, each member independently selected from C, N, O, S, CH, $CH_2$, NH;
    is saturated, partially unsaturated or aromatic;
  wherein A is substituted by one or more radicals selected from the group consisting of H, F, Cl, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH_2(CH_3)_2)_2$;
with the proviso that the compound is other than N-(4-methyl-6-hydroxy-pyrimidin-2-yl)-N'-(2-trifluoromethyl-phenyl)guanidine, N-[4,6-bis(methyl)pyrimidin-2-yl]-N'-[2-(trifluoromethyl)phenyl]guanidine or N-[(4-methyl)pyrimidin-2-yl]-N'-[2-(trifluoromethyl)phenyl]guanidine.

Yet another aspect of the present invention relates to a process for the preparation of a compound of formula I, which comprises reacting the aniline of formula (III) with a cyanamide of formula (IV):

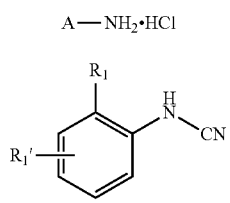

wherein A, $R_1$ and $R_1$' are as defined above.

DETAILED DESCRIPTION OF THE INVENTION

According to an embodiment of the first aspect, the present invention relates to compounds of formula I for use in the treatment of a condition mediated by Rho GTPase cell proteins, particularly by Rac1 cell proteins, wherein A is a ring system selected from

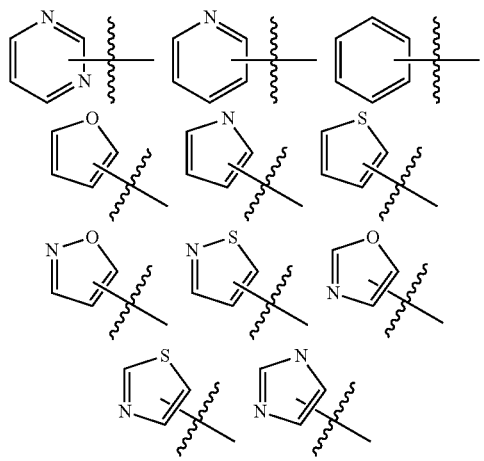

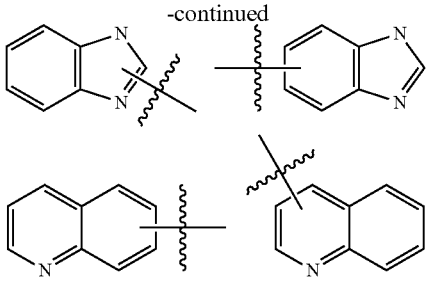

and wherein A is substituted as defined above, or a salt thereof, or any of its stereoisomeric forms or a mixture thereof, and the wavy line means the point of attachment of the ring to the adjacent nitrogen. More preferably, A is selected from the group consisting of a radical of pyridine, pyrimidine and phenyl; wherein A is substituted as defined above, or a salt thereof, or any of its stereoisomeric forms or a mixture thereof.

In another embodiment, the invention relates to the compounds of formula I for use in the treatment of a condition mediated by Rho GTPase cell proteins, particularly by Rac1 cell proteins, wherein A is a ring system selected from

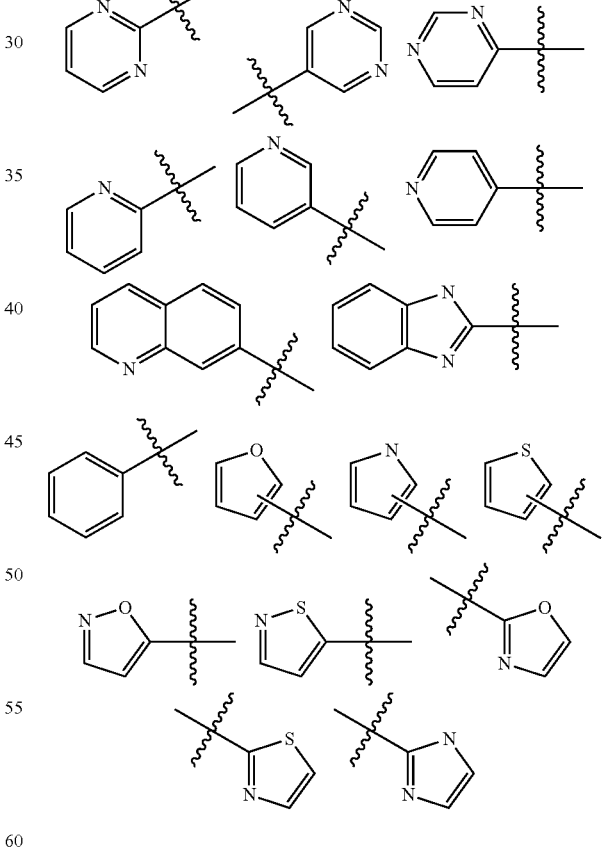

and wherein A is substituted by one or more radicals as defined above, or a salt thereof, or any of its stereoisomeric forms or a mixture thereof, and the wavy line means the point of attachment of the ring to the adjacent nitrogen. In a more preferred embodiment, the present invention relates to compounds of formula I for use in the treatment of a condition mediated by Rho GTPase cell proteins, particularly by Rac1 cell proteins, wherein R1 and R1' are as defined above; A is a ring system selected from

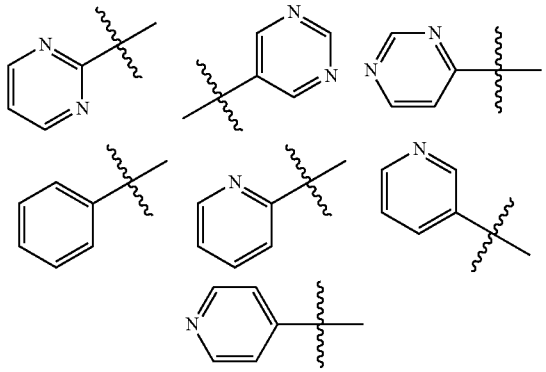

and wherein A is substituted by one or more radicals as defined above, or a salt thereof, or any of its stereoisomeric forms or a mixture thereof, and the wavy line means the point of attachment of the ring to the adjacent nitrogen.

According to an embodiment of the first aspect, the present invention relates to compounds of formula I for use in the treatment of a condition mediated by Rho GTPase cell proteins, particularly by Rac1 cell proteins, wherein A is selected from methyl, ethyl, n-propyl, iso-propyl, n-butyl, iso-butyl, sec-butyl, or n-pentyl, and wherein A is substituted as defined above, or a salt thereof, or any of its stereoisomeric forms or a mixture thereof.

In another embodiment, the invention relates to compounds of formula I for use in the treatment of a condition mediated by Rho GTPase cell proteins, particularly by Rac1 cell proteins, wherein the ring system of A, as defined in any of the embodiments above, is substituted by one or more radicals selected from the group consisting of H, F, Cl, Br, I, nitro, cyano, linear or branched $(C_1-C_6)$alkyl, halo-$(C_1-C_6)$alkyl, linear or branched $(C_2-C_6)$alkenyl, —$OR_2$, —$COR_2$, —$COOR_2$, —$OC(O)R_2$, —$C(O)NR_3R_4$, —$NR_3R_4$, —$R_5NHR_6$, —$SR_2$, —$SO$—$R_2$, —$SO_2$—$R_2$, and —$SO_2NR_3R_4$;
wherein
each $R_2$ independently represents H, methyl, ethyl, n-propyl, i-propyl, n-butyl, or t-butyl;
each $R_3$ independently represents H, methyl, ethyl, n-propyl, i-propyl, n-butyl, or t-butyl,
each $R_4$ independently represents H, methyl, ethyl, n-propyl, i-propyl, n-butyl, t-butyl, phenyl, pyridine or quinoline;
wherein the phenyl, pyridine and quinoline ring system is substituted by one or more radicals selected from H, methyl, ethyl, n-propyl, i-propyl, n-butyl, t-butyl, and $NH_2$;
$R_5$ and $R_6$ are independently selected from H, methyl, ethyl, n-propyl, i-propyl, n-butyl, or t-butyl;
or a salt thereof, or any of its stereoisomeric forms or a mixture thereof.

In another embodiment, the invention relates to compounds of formula I for use in the treatment of a condition mediated by Rho GTPase cell proteins, particularly by Rac1 cell proteins, wherein the ring system of A, as defined in any of the embodiments above, is substituted by one or more radicals selected from the group consisting of H, F, Cl, Br, I, nitro, cyano, methyl, ethyl, n-propyl, i-propyl, n-butyl, t-butyl, —$CF_3$, —$CH_2CF_3$, linear or branched $(C_2-C_6)$alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —$N(CH_3)_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NH$ $CH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH_2(CH_3)_2)_2$;
or a salt thereof, or any of its stereoisomeric forms or a mixture thereof.

Another embodiment relates to compounds of formula I for use in the treatment of a condition mediated by Rho GTPase cell proteins, particularly by Rac1 cell proteins, wherein $R_1$ and $R_1'$ are independently selected from H, $CF_3$, $NH_2$, methyl, ethyl, F, Cl, Br, I, and OH; or a salt thereof, or any of its stereoisomeric forms or a mixture thereof; with the proviso that at least one of $R_1$ and $R_1'$ are different of H. Preferred are those compounds of formula I wherein $R_1$ is $CF_3$ and $R_1'$ is H.

Particularly preferred are those compounds of formula Ia

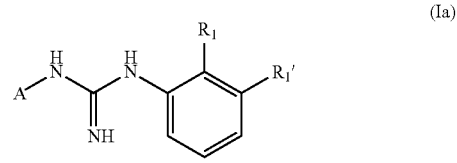

(Ia)

wherein $R_1$ and $R_1'$ are independently selected from H, $CF_3$, $NH_2$, methyl, ethyl, F, Cl, Br, I, and OH; with the proviso that when $R_1$ is H then $R_1'$ is different of H, and viceversa;
A is as defined in any of the embodiments above; or a salt thereof, or any of its stereoisomeric forms or a mixture thereof; for use in the treatment of a condition mediated by Rho GTPase cell proteins, particularly by Rac1 cell proteins.

Also preferred are those compounds of formula Ia wherein $R_1'$ is H, and $R_1$ is selected from $CF_3$, $NH_2$, methyl and ethyl; being particularly preferred when $R_1'$ is H, and $R_1$ is $CF_3$; for use in the treatment of a condition mediated by Rho GTPase cell proteins, particularly by Rac1 cell proteins.

According to a particular embodiment of this first aspect, the invention provides compounds of formula Ia for use in the treatment of a condition mediated by Rho GTPase cell proteins, particularly by Rac1 cell proteins, wherein
$R_1$ and $R_1'$ are independently selected from H, $CF_3$, $NH_2$, methyl, ethyl, F, Cl, Br, I, and OH; with the proviso that when $R_1$ is H then $R_1'$ is different of H, and viceversa;
A is a radical of one of the known heterocyclic ring systems with 1-2 rings, wherein each of the rings forming the ring system
has 5-7 members, each member independently selected from C, N, O, S, CH, $CH_2$, NH;
is saturated, partially unsaturated or aromatic;
wherein A is substituted by one or more radical selected from the group consisting of H, F, Cl, Br, I, nitro, cyano, methyl, ethyl, n-propyl, i-propyl, n-butyl, t-butyl, —$CF_3$, —$CH_2CF_3$, linear or branched $(C_2-C_6)$alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —$N(CH_3)_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NH$ $CH_2CH_3$, —$SO_2N$ $(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH_2(CH_3)_2)_2$.

or a salt or solvate thereof, or any of its stereoisomeric forms or a mixture thereof.

According to another embodiment, the invention provides compounds of formula Ia for use in the treatment of a condition mediated by Rho GTPase cell proteins, particularly by Rac1 cell proteins, wherein $R_1$ and $R_1'$ are independently selected from H, $CF_3$, $NH_2$, methyl, and ethyl; with the proviso that when $R_1$ is H then $R_1'$ is different of H, and viceversa;

A is selected from the group consisting of a radical of pyrimidine, pyridine, quinoline, imidazole, benzoimidazole and pyrrole, being particularly preferred those compounds wherein A is a radical of pyrimidine;

wherein A is substituted by one or more radical selected from the group consisting of H, F, Cl, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH(CH_3)_2)_2$; or a salt thereof, or any of its stereoisomeric forms or a mixture thereof.

According to another particular embodiment, the invention provides compounds of formula Ia for use in the treatment of a condition mediated by Rho GTPase cell proteins, particularly by Rac1 cell proteins, wherein $R_1$ and $R_1'$ are independently selected from H, $CF_3$, $NH_2$, methyl, and ethyl; with the proviso that at least one of $R_1$ and $R_1'$ are different of H; and A is a phenyl radical substituted by one or more radicals selected from the group consisting of H, F, Cl, Br, I, nitro, cyano, methyl, ethyl, n-propyl, propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH(CH_3)_2)_2$; or a salt thereof, or any of its stereoisomeric forms or a mixture thereof.

According to another particular embodiment, the invention provides compounds of formula Ia for use in the treatment of a condition mediated by Rho GTPase cell proteins, particularly by Rac1 cell proteins, wherein $R_1$ and $R_1'$ are independently selected from H, $CF_3$, $NH_2$, methyl, and ethyl; with the proviso that at least one of $R_1$ and $R_1'$ are different of H; and A is a linear or branched ($C_1$-$C_6$)alkyl radical, preferably selected from methyl, ethyl, n-propyl, iso-propyl, n-butyl, iso-butyl, sec-butyl, or n-pentyl, which is substituted by one or more radicals selected from the group consisting of H, F, Cl, Br, I, nitro, cyano, —$CF_3$, —$CH_2CF_3$, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH(CH_3)_2)_2$; or a salt thereof, or any of its stereoisomeric forms or a mixture thereof.

In a particularly preferred embodiment of this first aspect, the invention relates to the compounds of formula I which are selected from:

N-pyrimidin-2-yl-N'-[2-(trifluoromethyl)phenyl]guanidine (1);

N-(4-ethyl-6-methylpyrimidin-2-yl)-N'-[2-(trifluoromethyl)phenyl]guanidine (2);

N-(4-methyl-6-propylpyrimidin-2-yl)-N'-[2-(trifluoromethyl)phenyl]guanidine (3);

N-(4-isopropyl-6-methylpyrimidin-2-yl)-N'-[2-(trifluoromethyl)phenyl]guanidine (4);

N-(4-butyl-6-methylpyrimidin-2-yl)-N'-[2-(trifluoromethyl)phenyl]guanidine (5);

N-(4-tert-butyl-6-methylpyrimidin-2-yl)-N'-[2-(trifluoromethyl)phenyl]guanidine (6);

N-(4,6-diaminopyrimidin-2-yl)-N'-[2-(trifluoromethyl)phenyl]guanidine (7);

N-(4,6-dichloropyrimidin-2-yl)-N'-[2-(trifluoromethyl)phenyl]guanidine (8);

N-(4,6-difluoropyrimidin-2-yl)-N'-[2-(trifluoromethyl)phenyl]guanidine (9);

N-[4-methyl-6-(trifluoromethyl)pyrimidin-2-yl]-N'-[2-(trifluoromethyl)phenyl]guanidine (10);

N-(4-cyano-6-methylpyrimidin-2-yl)-N'-[2-(trifluoromethyl)phenyl]guanidine (11), N-(5-methylpyrimidin-2-yl)-N'-[2-(trifluoromethyl)phenyl]guanidine (12);

N-(4-chloro-6-methylpyrimidin-2-yl)-N'-[2-(trifluoromethyl)phenyl]guanidine (13), N-(4-fluoro-6-methylpyrimidin-2-yl)-N'-[2-(trifluoromethyl)phenyl]guanidine (14), N-(4-fluoropyrimidin-2-yl)-N'-[2-(trifluoromethyl)phenyl]guanidine (15);

N-(5-fluoropyrimidin-2-yl)-N'-[2-(trifluoromethyl)phenyl]guanidine (16);

N-[4,6-bis(trifluoromethyl)pyrimidin-2-yl]-N'-[2-(trifluoromethyl)phenyl]guanidine (17);

N-(4,6-dicyanopyrimidin-2-yl)-N'-[2-(trifluoromethyl)phenyl]guanidine (18);

N-pyridin-2-yl-N'-[2-(trifluoromethyl)phenyl]guanidine (19);

N-pyridin-3-yl-N'-[2-(trifluoromethyl)phenyl]guanidine (20);

N-pyridin-4-yl-N'-[2-(trifluoromethyl)phenyl]guanidine (21);

N-pyrimidin-4-yl-N'-[2-(trifluoromethyl)phenyl]guanidine (22);

N-pyrimidin-5-yl-N'-[2-(trifluoromethyl)phenyl]guanidine (23);

N-(4,6-dimethylpyridin-2-yl)-N'-[2-(trifluoromethyl)phenyl]guanidine (24);

N-(3,5-dimethylphenyl)-N'-[2-(trifluoromethyl)phenyl]guanidine (25);

N-(2,6-dimethylpyridin-4-yl)-N'-[2-(trifluoromethyl)phenyl]guanidine (26);

N-phenyl-N'-[2-(trifluoromethyl)phenyl]guanidine (27);

2-[(imino{[2-(trifluoromethyl)phenyl]amino}methyl)amino]-N,N-dimethylbenzenesulfonamide (28);

2-[(imino{[2-(trifluoromethyl)phenyl]amino}methyl)amino]-N,N-diethylbenzenesulfonamide (29);

2-[(imino{[2-(trifluoromethyl)phenyl]amino}methyl)amino]-N,N-dipropylbenzenesulfonamide (30);

2-[(imino{[2-(trifluoromethyl)phenyl]amino}methyl)amino]-N,N-dibutylbenzenesulfonamide (31);

3-[(imino{[2-(trifluoromethyl)phenyl]amino}methyl)amino]-N,N-dimethylbenzenesulfonamide (32);

3-[(imino{[2-(trifluoromethyl)phenyl]amino}methyl) amino]-N,N-diethylbenzenesulfonamide (33);
3-[(imino{[2-(trifluoromethyl)phenyl]amino}methyl) amino]-N,N-dipropylbenzenesulfonamide (34);
3-[(imino{[2-(trifluoromethyl)phenyl]amino}methyl) amino]-N,N-dibutylbenzenesulfonamide (35);
4-[(imino{[2-(trifluoromethyl)phenyl]amino}methyl) amino]-N,N-dimethylbenzenesulfonamide (36);
4-[(imino{[2-(trifluoromethyl)phenyl]amino}methyl) amino]-N,N-diethylbenzenesulfonamide (37);
4-[(imino{[2-(trifluoromethyl)phenyl]amino}methyl) amino]-N,N-dipropylbenzenesulfonamide (38);
4-[(imino{[2-(trifluoromethyl)phenyl]amino}methyl) amino]-N,N-dibutylbenzenesulfonamide (39);
N-(2-nitrophenyl)-N'-[2-(trifluoromethyl)phenyl]guanidine (40);
N-(3-nitrophenyl)-N'-[2-(trifluoromethyl)phenyl]guanidine (41);
N-(4-nitrophenyl)-N'-[2-(trifluoromethyl)phenyl]guanidine (42);
N-2-thienyl-N'-[2-(trifluoromethyl)phenyl]guanidine (43);
N-3-thienyl-N'-[2-(trifluoromethyl)phenyl]guanidine (44);
N-1H-pyrrol-2-yl-N'-[2-(trifluoromethyl)phenyl]guanidine (45);
N-1H-pyrrol-3-yl-N'-[2-(trifluoromethyl)phenyl]guanidine (46);
N-2-furyl-N'-[2-(trifluoromethyl)phenyl]guanidine (47);
N-3-furyl-N'-[2-(trifluoromethyl)phenyl]guanidine (48);
N-1,3-oxazol-2-yl-N'-[2-(trifluoromethyl)phenyl]guanidine (49);
N-1,3-thiazol-2-yl-N'-[2-(trifluoromethyl)phenyl]guanidine (50);
N-1H-imidazol-2-yl-N'-[2-(trifluoromethyl)phenyl]guanidine (51);
N-isoxazol-5-yl-N'-[2-(trifluoromethyl)phenyl]guanidine (52);
N-1H-benzimidazol-2-yl-N'-[2-(trifluoromethyl)phenyl] guanidine (53);
N-(3,4-dimethylisoxazol-5-yl)-N'-[2-(trifluoromethyl)phenyl]guanidine (54);
N-(2-aminophenyl)-N'-(4,6-dimethylpyrimidin-2-yl)guanidine (55);
N-(4,6-dimethylpyrimidin-2-yl)-N'-(3-ethylphenyl)guanidine (56);
1-(4-(4-amino-2-methylquinolin-7-ylamino)pyrimidin-2-yl)-3-(2-(trifluoromethyl)phenyl)guanidine (57);
N-(4-amino-2-methylquinolin-7-yl)-N'-[2-(trifluoromethyl) phenyl]guanidine (58);
N-quinolin-7-yl-N'-[2-(trifluoromethyl)phenyl]guanidine (59);
N-methyl-N'-[2-(trifluoromethyl)phenyl]guanidine (60);
N-ethyl-N'-[2-(trifluoromethyl)phenyl]guanidine (61);
N-propyl-N'-[2-(trifluoromethyl)phenyl]guanidine (62);
N-butyl-N'-[2-(trifluoromethyl)phenyl]guanidine (63);
N-(2-methylphenyl)-N'-[2-(trifluoromethyl)phenyl]guanidine (64); and
N-[4,6-bis(methyl)pyrimidin-2-yl]-N'-[2-(trifluoromethyl) phenyl]guanidine (65).

Particularly preferred compounds of formula I are N-[4,6-bis(methyl)pyrimidin-2-yl]-N'-[2-(trifluoromethyl)phenyl]guanidine (65), N-(3,5-dimethylphenyl)-N'-[2-(trifluoromethyl)phenyl]guanidine (25), N-phenyl-N'-[2-(trifluoromethyl)phenyl]guanidine (27), N-(3-nitrophenyl)-N'-[2-(trifluoromethyl)phenyl]guanidine (41), N-[4-methyl-6-(trifluoromethyl)pyrimidin-2-yl]-N'-[2-(trifluoromethyl) phenyl]guanidine (10) and N-(2-methylphenyl)-N'-[2-(trifluoromethyl)phenyl]guanidine (64)).

Throughout the present specification, by the term "treatment" is meant eliminating, reducing or ameliorating the cause, the effects or progression of a condition; and includes a reduction in the rate of progress, a halt in the rate of progress, amelioration of the condition, and cure of the condition.

Treatment as a prophylactic measure (e.g., prophylaxis) is also included. The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy. For purposes of this invention treatment includes, but is not limited to, alleviation, amelioration or elimination of one or more symptoms of the condition; diminishment of the extent of the condition; stabilized (i.e. not worsening) state of condition; delay or slowing of condition progression; amelioration or palliation of the condition state; and remission of the condition (whether partial or total).

As it is shown below, the compounds of formula I are Rho GTPase cell protein, more specifically Rac1 cell protein, inhibitors, being useful in the treatment of a condition mediated by Rho GTPase cell protein, preferably a condition mediated by Rac1 cell protein.

The term "a disease mediated by Rac1 cell protein", as used herein pertains to a condition in which Rac1 cell protein and/or the action of Rac1 is important or necessary, e.g., for the onset, progress, expression, etc. of that condition.

Since Rho-GTPases kinases are known to have a central role in the cell cycle, and in particular Rac1, in a preferred embodiment of the present invention the diseases, conditions and/or disorders, which can be prevented, ameliorated or treated with the compounds of the present invention are proliferative diseases. A disease is considered to benefit from reduced Rho-GTPase, in particular Rac1 activity, if a reduction of Rac1 activity of at least 10%, preferably of at least 20%, preferably of at least 30%, leads to an improvement of at least one clinical indicator of that disease. Examples of such indicators are proliferation rate, which is preferably reduced, cellular differentiation, which is preferably induced etc.

It is further preferred that the proliferative diseases are selected from the group consisting of precancerosis; dysplasia; metaplasia; carcinomas of the gastrointestinal or colorectal tract, liver, pancreas, kidney, bladder, prostate, endometrium, ovary, testes, melanoma, dysplastic oral mucosa, invasive oral cancers, small cell and non-small cell lung carcinomas, hormone-dependent breast cancers, hormone-independent breast cancers, transitional and squamous cell cancers, neurological malignancies including neuroblastoma, gliomas, glioblastoma, astrocytomas, osteosarcomas, soft tissue sarcomas, hemangioamas, endocrinological tumors, hematologic neoplasias including leukemias, lymphomas, and other myeloproliferative and lymphoproliferative diseases, carcinomas in situ, hyperplastic lesions, adenomas, fibromas, histiocytosis, chronic inflammatory proliferative diseases, vascular proliferative diseases and virus-induced proliferative diseases, skin diseases characterized by hyperproliferation of keratinocytes and/or T cells. Particular preferred diseases treatable with the compounds of the present invention are glioblastoma, colorectal, ovarian, prostatic and gastric cancers and adenocarcinomas, more preferably invasive adenocarcinomas.

Thus, the present invention also provides active compounds which are antiproliferative agents. The term "antiproliferative agent" as used herein, refers to a compound which treats a proliferative condition (i.e., a compound which is useful in the treatment of a proliferative condition).

The terms "cell proliferation", "proliferative condition", "proliferative disorder", and "proliferative disease", are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumors (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human. Preferably, the subject is a human.

Furthermore, the present invention covers all possible combinations of particular and preferred groups described hereinabove.

The treatment defined hereinbefore may be applied as a sole therapy or may involve, in addition to the compound of the invention, conventional surgery or radiotherapy or chemotherapy.

Also it is provided a compound of formula I for use in the treatment of a condition mediated by Rac1 cell proteins, wherein the treatment comprises administering to a subject simultaneously, sequentially or separately at least one compound of formula I as defined above and
  i) one or more anticancer agents, preferably selected from gemcitabine, paclitaxel, docetaxel, capecitabine, decitabin, carboplatin, cisplatin, vinorelbine, irinotecan, doxorubicin, dacarbazine, rituximab or a derivative thereof;
  ii) radiotherapy;
  iii) conventional surgery;
  iv) or mixtures thereof.

Further, it is also provided a method of treatment of a condition mediated by Rac1 cell proteins comprising administering simultaneously, sequentially or separately, to a human or animal body suffering such condition a therapeutically effective amount of at least one compound of formula I as defined above and
  i) one or more anticancer agents, preferably selected from gemcitabine, paclitaxel, docetaxel, capecitabine, decitabin, carboplatin, cisplatin, vinorelbine, irinotecan, doxorubicin, dacarbazine, rituximab or a derivative thereof;
  ii) radiotherapy;
  iii) conventional surgery;
  iv) or mixtures thereof.

Further, it is provided the use of a combined preparation comprising at least one compound of formula I and
  i) one or more anticancer agents, preferably selected from gemcitabine, paclitaxel, docetaxel, capecitabine, decitabin, carboplatin, cisplatin, vinorelbine, irinotecan, doxorubicin, dacarbazine, rituximab or a derivative thereof;
  ii) radiotherapy;
  iii) conventional surgery;
  iv) or mixtures thereof;
for the treatment of a condition mediated by Rac1 cell proteins.

Alternatively, it is provided a compound of formula I for use in a treatment of a condition mediated by Rac1 cell proteins in a combined therapy which comprises the use of a compound of formula I and
  i) one or more anticancer agents, preferably selected from gemcitabine, paclitaxel, docetaxel, capecitabine, decitabin, carboplatin, cisplatin, vinorelbine, irinotecan, doxorubicin, dacarbazine, rituximab or a derivative thereof;
  ii) radiotherapy;
  iii) conventional surgery;
  iv) or mixtures thereof.

As mentioned above, the present invention also provides new compounds of formula II.

It is noted that general formula I encompasses those compounds of formula II. Therefore, compounds of formula II are also useful for use in the treatment of a condition mediated by Rho GTPase cell proteins, particularly by Rac1 cell proteins, According to an embodiment, it is provided new compounds of formula II wherein A is a phenyl radical substituted by one or more radicals selected from the group consisting of H, F, Cl, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH(CH_3)_2)_2$; or a salt thereof, or any of its stereoisomeric forms or a mixture thereof.

Another embodiment relates to compounds of formula II wherein A is a heterocyclic ring system with 1-2 rings, wherein each of the rings forming the ring system
  has 5-7 members, each member independently selected from C, N, O, S, CH, $CH_2$, NH;
  is saturated, partially unsaturated or aromatic;
  wherein A is substituted by one or more radicals selected from the group consisting of H, F, Cl, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2N(CH_3)_2$, —$SO_2N(CH_2CH_3)_2$, —$SO_2N(CH_2CH_2CH_3)_2$, —$SO_2N(CH_2CH_2CH_2CH_3)_2$ and —$SO_2N(CH_2CH(CH_3)_2)_2$; or a salt thereof, or any of its stereoisomeric forms or a mixture thereof;
  with the proviso that the compound is other than N-(4-methyl-6-hydroxy-pyrimidin-2-yl)-N'-(2-trifluoromethyl-phenyl)guanidine, N-[4,6-bis(methyl)pyrimidin-2-yl]-N'-[2-

(trifluoromethyl)phenyl]guanidine or N-[(4-methyl)pyrimidin-2-yl]-N'-[2-(trifluoromethyl)phenyl]guanidine.

In a more preferred embodiment, the present invention provides compounds of formula II wherein A is selected from the group consisting of a radical of pyrimidine, pyridine, quinoline, imidazole, benzoimidazole and pyrrole; wherein A is substituted by one or more radicals selected from the group consisting of H, F, Cl, Br, I, nitro, cyano, methyl, ethyl, n-propyl, i-propyl, n-butyl, t-butyl, —CF$_3$, —CH$_2$CF$_3$, linear or branched (C$_2$-C$_6$)alkenyl, —OH, —OCH$_3$, —OCH$_2$CH$_3$, —COH, —COCH$_3$, —COOH, —COOCH$_3$, —COOCH$_2$CH$_3$, —OC(O)H, —OC(O)CH$_3$, —C(O)NH$_2$, —NH$_2$, —NHCH$_3$, —N(CH$_3$)$_2$, —CH$_2$NH$_2$, —CH$_2$NHCH$_3$, —SH$_2$, —SO—CH$_3$, —SO$_2$—CH$_3$, —SO$_2$NH$_2$, —SO$_2$NHCH$_3$, —SO$_2$NHCH$_2$CH$_3$, —SO$_2$N(CH$_3$)$_2$, —SO$_2$N(CH$_2$CH$_3$)$_2$, —SO$_2$N(CH$_2$CH$_2$CH$_3$)$_2$, —SO$_2$N(CH$_2$CH$_2$CH$_2$CH$_3$)$_2$ and —SO$_2$N(CH$_2$CH(CH$_3$)$_2$)$_2$; or a salt thereof, or any of its stereoisomeric forms or a mixture thereof;

with the proviso that the compound is other than N-(4-methyl-6-hydroxy-pyrimidin-2-yl)-N'-(2-trifluoromethyl-phenyl)guanidine, N-[4,6-bis(methyl)pyrimidin-2-yl]-N'-[2-(trifluoromethyl)phenyl]guanidine or N-[(4-methyl)pyrimidin-2-yl]-N'-[2-(trifluoromethyl)phenyl]guanidine.

Particularly preferred are those compounds of formula II wherein is a radical of pyrimidine; being the radical A substituted by one or more radicals selected from the group consisting of H, F, Cl, Br, I, nitro, cyano, methyl, ethyl, n-propyl, i-propyl, n-butyl, t-butyl, —CF$_3$, —CH$_2$CF$_3$, linear or branched (C$_2$-C$_6$)alkenyl, —OH, —OCH$_3$, —OCH$_2$CH$_3$, —COH, —COCH$_3$, —COOH, —COOCH$_3$, —COOCH$_2$CH$_3$, —OC(O)H, —OC(O)CH$_3$, —C(O)NH$_2$, —NH$_2$, —NHCH$_3$, —N(CH$_3$)$_2$, —CH$_2$NH$_2$, —CH$_2$NHCH$_3$, —SH$_2$, —SO—CH$_3$, —SO$_2$—CH$_3$, —SO$_2$NH$_2$, —SO$_2$NHCH$_3$, —SO$_2$NHCH$_2$CH$_3$, —SO$_2$N(CH$_3$)$_2$, —SO$_2$N(CH$_2$CH$_3$)$_2$, —SO$_2$N(CH$_2$CH$_2$CH$_3$)$_2$, —SO$_2$N(CH$_2$CH$_2$CH$_2$CH$_3$)$_2$ and —SO$_2$N(CH$_2$CH(CH$_3$)$_2$)$_2$; or a salt thereof, or any of its stereoisomeric forms or a mixture thereof;

with the proviso that the compound is other than N-(4-methyl-6-hydroxy-pyrimidin-2-yl)-N'-(2-trifluoromethyl-phenyl)guanidine, N-[4,6-bis(methyl)pyrimidin-2-yl]-N'-[2-(trifluoromethyl)phenyl]guanidine or N-[(4-methyl)pyrimidin-2-yl]-N'-[2-(trifluoromethyl)phenyl]guanidine.

Compounds N-(3,5-dimethylphenyl)-N'-[2-(trifluoromethyl)phenyl]guanidine (25), N-phenyl-N'-[2-(trifluoromethyl)phenyl]guanidine (27), N-(3-nitrophenyl)-N'-[2-(trifluoromethyl)phenyl]guanidine (41), N-[4-methyl-6-(trifluoromethyl)pyrimidin-2-yl]-N'-[2-(trifluoromethyl)phenyl]guanidine (10) and N-(2-methylphenyl)-N'-[2-(trifluoromethyl)phenyl]guanidine (64) are specific examples of preferred compounds of formula II.

When the compounds according to the present invention are in the form of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts.

In addition to salt forms, the present invention provides compounds which are in a prodrug form. Prodrugs of the compounds described herein are those compounds which, upon administration to a subject, undergo chemical conversion by metabolic or chemical processes to yield a compound of formula (I), and/or a salt and/or solvate thereof. A prodrug is a pharmacologically active or inactive compound that is modified chemically through in vivo physiological action, such as hydrolysis, metabolism and the like, into a compound of this invention following administration of the prodrug to a patient. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme. The suitability and techniques involved in making and using prodrugs are well known by those skilled in the art.

All stereoisomers of the compounds of the present invention, such as those, for example, which may exist due to asymmetric carbons on any of the substituents, including enantiomeric forms (which may exist even in the absence of asymmetric carbons) and diastereomeric forms, are contemplated and within the scope of the preferred embodiments. Also individual stereoisomers which may, for example, be substantially free of other isomers, or may be admixed, for example, as racemates or with all other selected stereoisomers, are intended to be within the scope of the present invention.

Certain compounds of the present invention can exist in unsolvated forms as well as in solvated forms, including hydrated forms, and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The present invention also relates to a pharmaceutical composition that comprises a compound of the present invention (or a pharmaceutically acceptable salt thereof) according to formula II and one or more pharmaceutically acceptable carriers. The carriers must be "pharmaceutically acceptable" in the sense of being compatible with the other ingredients of the composition and not deleterious to the recipients thereof.

The present invention also relates to pharmaceutical compositions comprising at least one compound of formula II as defined herein, at least one or more further therapeutically active substance and one or more pharmaceutically acceptable carriers.

The term "pharmaceutically acceptable" as used herein pertains to compounds, materials, compositions, and/or dosage forms which are, within the scope of sound medical judgment, suitable for use in contact with the tissues of a subject (e. g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The term "therapeutically effective amount," as used herein, pertains to that amount of an active compound, or a material, composition or dosage form comprising an active compound, which is effective for producing some desired therapeutic effect.

The compounds of the present invention can be administered in the form of any pharmaceutical formulation, the nature of which, as it is well known, will depend upon the nature of the active compound and its route of administration. Any route of administration may be used, for example oral, parenteral, nasal, ocular, rectal and topical administration. The person skilled in the art will establish, considering the available knowledge, the necessary parameters and excipients.

The compounds of the present invention may be used in a substantially similar manner to other known anti-tumor agents for treating (both chemopreventively and therapeutically) various malignant diseases. The anti-tumour dose to be administered, whether a single dose, multiple dose, or a daily dose, will of course vary with the particular compound employed, the chosen route of administration, the body weight and body surface of the recipient, the type of tumour, and the patient's physical condition and disease stage, among other factors. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological or physiological effects. A skilled physician in the art of cancer treatment will be able to ascertain, appropriate protocols for the effective administration of the compounds of the preferred embodiments. A representative example of a suitable dosage range is from about 0.01 mg/Kg to about 100 mg/Kg per day, which can be administered as single or divided doses.

Also encompassed within the scope of the invention is a process for the preparation of a compound of formula I as described above, which comprises reacting the aniline of formula (III) with a cyanamide of formula (IV):

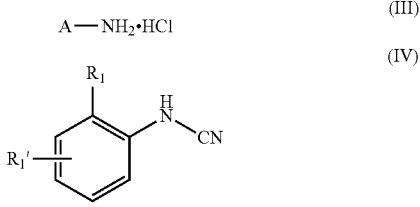

wherein A, $R_1$ and $R_1$ are as defined in claim 1.

It should be noted that the general procedures are shown as it relates to preparation of compounds having unspecified stereochemistry. However, such procedures are generally applicable to those compounds of a specific stereochemistry, e.g., where the stereochemistry at a stereogenic center is (S) or (R). In addition, the compounds having one stereochemistry (e.g., (R)) may often be utilized to produce those having opposite stereochemistry (i.e., (S)) using well known methods, for example, by inversion. The same applies for Z/E enantiomers.

The term "($C_1$-$C_6$)alkyl" as used herein refers to a saturated branched or linear hydrocarbon chain with 1 to 6 hydrocarbon atoms. Preferably "($C_1$-$C_6$)alkyl" is an unsubstituted group selected from methyl, ethyl, propyl, isopropyl, butyl, isobutyl, s-butyl and t-butyl.

The term "($C_1$-$C_6$)-alkoxy" as used herein refers to a saturated branched or linear hydrocarbon chain with 1 to 6 hydrocarbon atoms (i.e. ($C_1$-$C_6$)alkyl groups as defined above) linked to an oxygen, thus ($C_1$-$C_6$)alkyl-O. Preferably "($C_1$-$C_6$)-alkoxy" is an unsubstituted group selected from methoxy, ethoxy, propoxy, isopropoxy, butoxy, isobutoxy, s-butoxy, and t-butoxy.

The term "halogen" is meant to include fluorine, chlorine, bromine and iodine.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention.

The following examples and drawings are provided by way of illustration, and they are not intended to be limiting of the present invention. Furthermore, the present invention covers all possible combinations of particular and preferred embodiments described herein.

EXAMPLES

Figure 1:
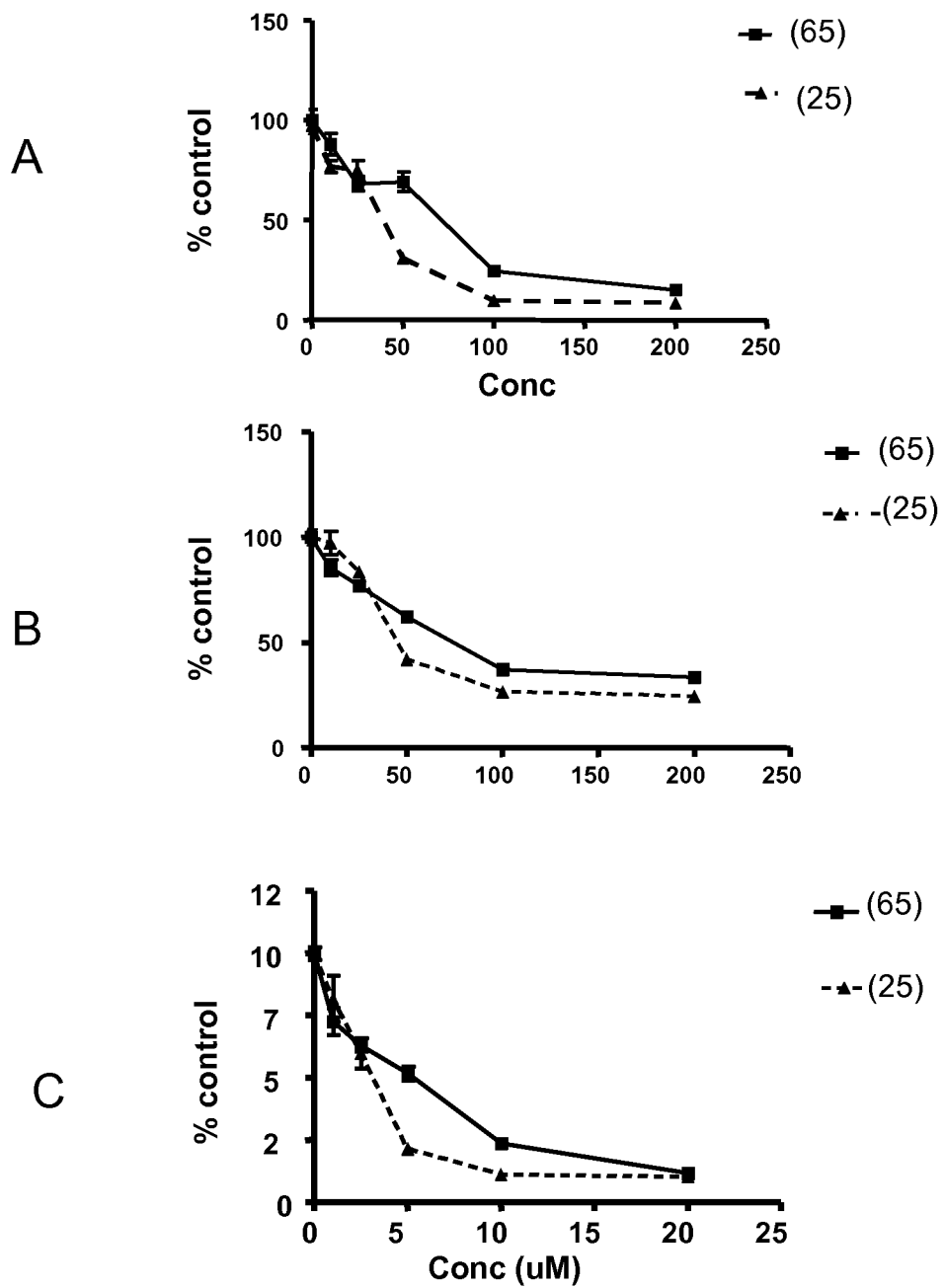
FIG. 1: Antiproliferative effect of compounds (65) and (25) over LN229 (A), MDA-MB-231 (B) and F3II (C).

All reagents were commercially available. Melting points were measured with an Electrothermal IA9000 Series (with a temperature gradient of 1° C./minute) and were uncorrected. Chromatograpy purifications were performed in a flash column chromatograpy apparatus Teledyne Isco CombiFlash Companion equipment with Redisep detachable columns, using mixtures of solvents with ascending polarity as mobile phase. $^1$H and $^{13}$C NMR spectra were recorded on a Bruker ADVANCE DPX-400. Microanalysis was carried out by UNYMFOR (CONICET-FCEyN). Low resolution mass spectra were recorded on a Shimadzu QP2010 apparatus. IR spectra were recorded on a Nicolet Impact 400 apparatus.

Example 1

Preparation of N-(3,5-dimethylphenyl)-N'-[2-(trifluoromethyl)phenyl]guanidine (25)

The title compound was obtained according to the following method:

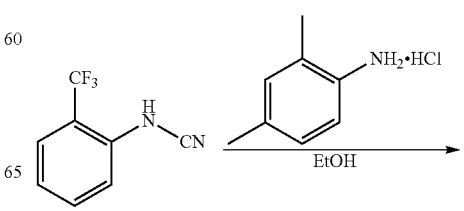

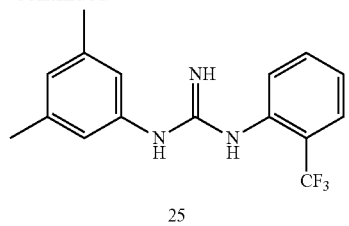

An equimolar amount of compounds chlorohydrate of 3,5-dimethylaniline solution (126 mg, 0.80 mmol) and N-(2-(trifluoromethyl)phenyl)cianamide (149 mg, 0.80 mmol) in absolute ethanol (2.5 mL) was heated to reflux with stirred for 16 h. An aqueous solution of NaOH (0.5 M, 2.2 mL) was added until pH 9. The mixture was extracted with dichloromethane (3×3 mL). Organic phases were dried with $Na_2SO_4$ and filtered. The solvent was evaporated to obtain 225 mg (92% yield) of the title compound. Crude product was purified by column chromatography with a hexane:ethyl acetate gradient (1:4 to 0:10) in presence of 0.01% of triethylamine to obtaining 138 mg (56%) of pure compound (25) as a white solid, m.p. 127° C.

$^1$H RMN (400 MHz, $CDCl_3$) δ 7.63 (d, J=6.5 Hz, 1H), 7.44 (m, 1H), 7.08 (m, 2H), 6.84 (s, 2H), 6.77 (s, 1H), 4.27 (sa, 2H), 2.28 (s, 6H). $^{13}$C RMN (100 MHz, $CDCl_3$) δ 149.43, 147.59, 139.12, 132.79, 126.90 (q, J=5 Hz), 125.97, 125.31, 124.39 (q, J=272 Hz), 123.79 (q, J=29 Hz), 122.12, 120.36, 21.28. IR ($cm^{-1}$), 3476, 3372, 1648, 1560, 1316. MS (m/z, relative intensity) 307 ($M^+$, 23), 238 ($M^+$-$CF_3$, 6), 121 (100). Anal. Calcd. for $C_{16}H_{16}F_3N_3$: % C, 62.35; % H, 5.07; % N, 13.24. Found: % C, 62.53; % H, 5.25; % N, 13.67.

Compounds (27), (41) and (64) were prepared in a similar way reacting the corresponding aniline with the corresponding cianamide.

N-phenyl-N'-[2-(trifluoromethyl)phenyl]guanidine (27)

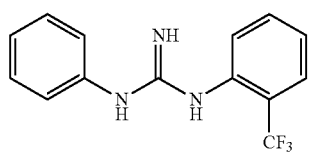 [SMILES: N=C(Nc1ccccc1)Nc1ccccc1C(F)(F)F]

Yield: 66%. White solid, m.p.=108-109° C. $^1$H RMN (400 MHz, $CDCl_3$) δ 7.62 (d, J=6.5 Hz, 1H), 7.44 (m, 1H), 7.30-7.21 (m, 4H), 7.08 (m, 2H), 4.92 (sa, 2H). $^{13}$C RMN (100 MHz, $CDCl_3$) δ 149.12, 147.04, 139.40, 132.86, 129.42, 126.94 (q, J=5 Hz), 125.18, 124.34 (q, J=272 Hz), 124.23, 123.79 (q, J=29 Hz), 122.55, 122.37. IR ($cm^{-1}$), 3379, 1647, 1549, 1318. MS (m/z, relative intensity) 279 ($M^+$, 26), 210 ($M^+$-$CF_3$, 7), 93 (100). Anal. Calcd. for $C_{14}H_{12}F_3N_3 \cdot 0.25H_2O$: % C, 59.26; % H, 4.44; % N, 14.81. Found: % C, 59.68; % H, 4.14; % N, 14.42.

N-(3-nitrophenyl)-N'-[2-(trifluoromethyl)phenyl]guanidine (41)

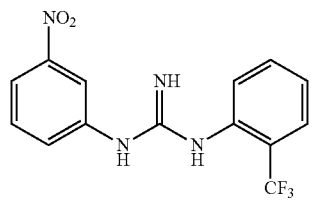 [SMILES: N=C(Nc1cccc([N+](=O)[O-])c1)Nc1ccccc1C(F)(F)F]

Yield: 60%. Yellow solid. $^1$H RMN (400 MHz, $CDCl_3$) δ 8.16 (s, 1H), 7.87 (d, J=7.9 Hz, 1H), 7.70 (m, 1H), 7.66 (d, J=7.6 Hz, 1H), 7.50 (t, J=7.7 Hz, 1H), 7.45 (t, J=7.9 Hz, 1H), 7.21-7.14 (m, 2H), 4.18 (sa, 2H). $^{13}$C RMN (100 MHz, $CD_3OD$ $CDCl_3$) δ 148.48, 148.29, 146.28, 142.09, 132.35, 128.96, 126.28 (q, J=5 Hz), 125.25, 124.45, 123.98 (q, J=272 Hz), 123.15 (q, J=29 Hz), 122.02, 115.98, 113.96. IR ($cm^{-1}$) 3437, 3336, 1656, 1520, 1318, 1105. MS (m/z, relative intensity) 324 ($M^+$, 75), 255 ($M^+$-$CF_3$, 48), 138 (100)

N-(2-methylphenyl)-N'-[2-(trifluoromethyl)phenyl]guanidine (64)

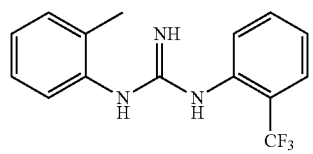 [SMILES: Cc1ccccc1NC(=N)Nc1ccccc1C(F)(F)F]

Yield: 87%. White solid, m.p.=129° C. $^1$H RMN (400 MHz, $CDCl_3$) δ 7.84 (d, J=7.9 Hz, 0.5H), 7.62 (d, J=7.8 Hz, 1H), 7.58 (d, J=7.9 Hz, 0.5H), 7.48 (m, 1.5H), 7.33 (d, J=7.6 Hz, 1H), 7.23-7.10 (m, 3.5H), 4.34 (sa, 2H), 2.29 (s, 3H). $^{13}$C RMN (100 MHz, $CD_3OD$-$CDCl_3$) δ 158.08, 151.61, 146.84, 137.71, 136.55, 134.10, 133.18, 132.83, 131.26, 127.12, 127.06 (q, J=5 Hz), 126.44, 126.32, 124.61 (q, J=29 Hz), 124.60 (q, J=272 Hz), 124.31, 123.06, 17.52. IR ($cm^{-1}$), 3438, 3409, 1645, 1592, 1316. MS (m/z, relative intensity) 293 ($M^+$, 35), 224 ($M^+$-$CF_3$, 6), 107 (100).

*Signals of two conformers are listed.

Preparation of N-[4,6-bis(methyl)pyrimidin-2-yl]-N'-[2-(trifluoromethyl)phenyl]guanidine (65) was performed following the method described in Chin. J. Chem. 2008, 1481[1].

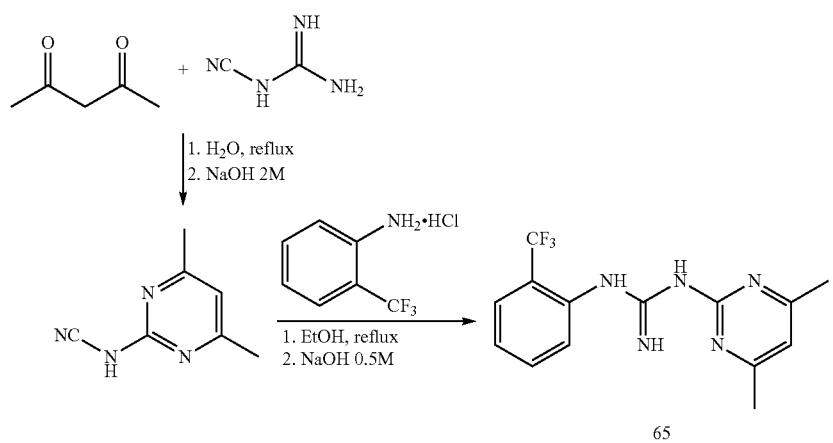

Cyanoguanidine (10 g, 0.12 mol), acetylacetone (17.2 mL, 0.17 mol) were treated with 2M NaOH (5.7 mL) in water (74 mL). The reaction mixture was stirred at 100° C. for 18 hs. The mixture was cooled down to room temperature and then to 0° C. under stirring for 2 hs. The crystallized solid was collected and dried at 50° C. to give 14.2 g of a pink solid. The crude solid was recrystallized from ethanol to give 10.2 g (58% yield) of N-(4.6-dimethylpyrimidin-2-yl)cyanamide as a white solid: mp 230-231° C., (lit[1]. 230-231° C.), $^1$H RMN (400 MHz, CDCl$_3$) δ 6.43 (s, 1H), 4.36 (bs, 1H), 3.26 (s, 6H), This intermediate was reacted with an equimolar amount of 2-(trifluoromethyl)aniline hydrochloride (13.6 g, 69.12 mmol) by refluxing the mixture in ethanol (150 mL) for 20 h. The mixture was allowed to reach room temperature and the pH was adjusted to 12-13 by addition of 0.5M NaOH aqueous solution (45 mL). The obtained solid was collected and recrystallized from ethanol:water (1:1) to yield 5.4 g of pure 65 as a white crystalline solid: m.p.=161-162° C. (lit[1]. 149-151° C.) $^1$H RMN (400 MHz, CDCl$_3$) δ 7.63 (d, J=7.6 Hz, 1H), 7.45 (t, J=7.6 Hz, 1H), 7.08 (m, 2H), 6.57 (s, 1H), 2.35 (s, 6H). $^{13}$C RMN (100 MHz, CDCl$_3$) δ 149.43, 147.59, 139.12, 132.79, 126.90 (q, J=5 Hz), 125.97, 125.31, 124.39 (q, J=272 Hz), 123.79 (q, J=29 Hz), 122.12, 120.36, 21.28. IR (cm$^{-1}$): 3443, 3213, 1662. HRMS (ESI) calcd for C$_{14}$H$_{15}$F$_3$N$_5$ (MH$^+$): 310.1274. found: 310.1265. Anal. Calcd. for C$_{14}$H$_{14}$F$_3$N$_5$.0.2H$_2$O: % C, 53.74; % H, 4.64; % N, 22.38. Found: % C, 54.03; % H, 4.57; % N, 21.98.

1-(4-methyl-6-(trifluoromethyl)pyrimidin-2-yl)-3-(2-trifluoromethyl)phenyl)guanidine (10)

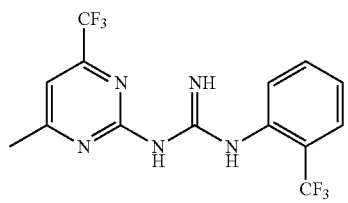 [SMILES: Cc1cc(C(F)(F)F)nc(NC(=N)Nc2ccccc2C(F)(F)F)n1]

This compound was prepared following the procedure described for compound (65) employing 1,1,1-trifluoro-2,4-pentanedione instead of 2,4-pentanedione (Chin. J. Chem. 2008, 1481). $^1$H RMN (400 MHz, CDCl$_3$) δ 7.67 (d, J=6.5 Hz, 1H), 7.51 (t, J=7.7 Hz, 1H), 7.19 (m, 2H), 6.96 (s, 1H), 2.43 (s, 3H). $^{13}$C RMN (100 MHz, CDCl$_3$) δ 171.23, 60.05, 155.21, 150.63, 146.03, 132.79, 126.97 (q, J=5 Hz), 125.52, 123.96 (q, J=272 Hz), 123.21 (m), 120.30 (q, J=275 Hz), 108.48, 24.30. IR (cm$^{-1}$) 3492, 3311, 1668, 1557, 1316. MS (m/z, relative intensity) 363 (M$^+$, 91), 362 (M$^+$-H, 100), 294 (M$^+$-CF$_3$, 92). Elemental Anal. Calcd. for C$_{14}$H$_{11}$F$_6$N$_5$: % C, 46.29, % H, 3.05, % N, 19.27. Found: % C, 46.32, % H, 3.04, % N, 18.98.

Example 2

Proliferation Assay

Cells were maintained in monolayer culture with the corresponding media, supplemented with 5% fetal bovine serum (FBS) previously inactivated with heat, 2 mM glutamine and 80 mg/ml gentamicine.

The cells were treated for 72 hours in the presence of FBS 10% with different doses of the compounds in 96 wells at a 2500 cell/well density. The cell growth was estimated by MTT test, for which to the cell monolayers was added MTT, incubated and resuspended in DMSO. Finally, the number of cells was estimated by measuring the absorbance values at 570 nm.

Compound (65) as a representative example of Rac1 inhibitor compounds according to the present invention was tested in cell proliferation assays performed with following cancer cell lines F3II (murine mammary carcinoma), 3LL (murine lung carcinoma), LN229 (human glioblastoma), MCF7 (human mammary carcinoma), H125 (human lung carcinoma), PC3 (human prostate adenocarcinoma) and MDA-MB-231 (human mammary carcinoma).

The level of proliferation was measured at 72 hours (h) after in vitro induction of compound (65) at different concentrations (200 μM, 100 μM, 50 μM, 25 μM, and 1 μM in presence of 10% fetal bovine serum (FBS) with the aim of determining the inhibitory concentration 50% (IC$_{50}$). The concentration producing 50% inhibition (IC50) was determined by non-linear regression function of GraphPad Prism5®. Results shown correspond to the average of three separate experiments. The IC$_{50}$ values are depicted in Table 1.

TABLE 1

IC$_{50}$ values (µM) of compound (65) tested in F3II, MCF7, 3LL, H125, LN229, PC3 and MDA-MB-231 cells

| | F3II | MCF7 | 3LL | H125 | LN229 | PC3 | MDA-MB-231 |
|---|---|---|---|---|---|---|---|
| (65) | 61 | 44 | 68 | 127 | 73 | 138 | 48 |

Other compounds according to formula I were also tested in LN229 cells. IC$_{50}$ values (µM) obtained are shown in Table 2.

TABLE 2

IC$_{50}$ values (µM) of compounds (25), (27), (41) and (64) tested in LN229 cells

| | Cpd. (25) | Cpd (27) | Cpd (41) | Cpd (64) |
|---|---|---|---|---|
| IC50 (µM) | 73 | 211 | 88 | 175 |

Compound (25) was also tested in F3II and MDA-MB-231 cells. IC$_{50}$ values (µM) obtained are shown in Table 3.

TABLE 3

IC$_{50}$ values (µM) of compound (25) tested in F3II and MDA-MB-231 cells.

| | F3II | MDA-MB-231 |
|---|---|---|
| (25) | 36 | 40 |

FIG. 1 show the doses-response curves of compounds (65) and (25) on the proliferative capacity of three cancer cell lines: (A) F3II (murine mammary carcinoma), (B) LN229 (human glioblastoma), (C) MDA-MB-231 (human mammary carcinoma).

Example 3

Inhibition of the Rac1 Activation Levels (Pull-Down)

This assay consists in the determination of inhibition power of the compounds of the invention over the intracellular active Rac1 levels (Rac-GTP). For determining the levels of Rac-GTP, the "Pull-Down" assay was used, which is based in the conformation bond of Rac-GTP to the p21 domain of PAK1 protein, which is the direct effector of Rac-GTP (Wanf H. et al.; J. Biol. Che. 2002, 277: 4541-4550).

Figure 2:
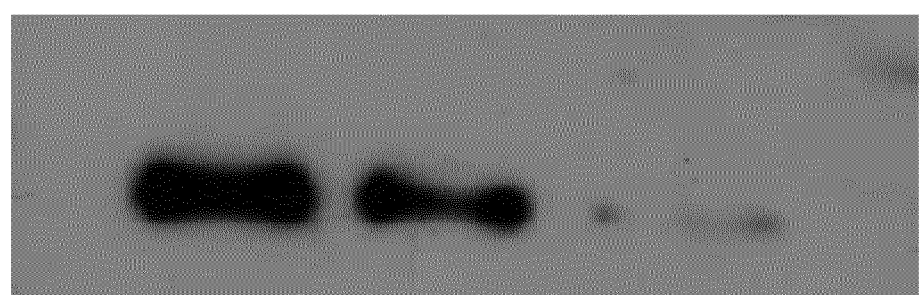
FIG. 2. Effect of compound (65) over Rac-Tiam complex.

Compounds (65) and (25) were tested in order to determine its inhibition power over the interaction Rac-Tiam. Thus, the precipitation affinity of Tiam with the recombinant protein GST-Rac was evaluated in presence of compound (65). FIG. 2 shows the effect of compound (65) over Rac-Tiam complex. It is shown the decrease of Rac interaction with the activator in presence of compound (65) in a Western Blot anti Tiam1 vs. control.

The inhibitory effect of compounds (25) and (65) over the intracellular active Rac levels were evaluated (Rac-GTP) by the "Pull-Down" assay.

LN229 cells (human glioblastoma) were seeded in 6-well cell culture plaques and were kept in absence of FBS for 48 hours (starvation). Afterwards, they were treated with compounds (25) and (65) and they were stimulated for 15 minutes with EGF (100 ng/ml), washed with phosphate buffered saline (PBS) at low temperature and lysated in a buffer containing 8 µg of the fusion protein GST-PBD, 20 nM Tris-HCl, pH 7.5, 1 nM DTT, 5 mM MgCl$_2$, 150 mM NaCl, 0.5% NP-40, 5 mM β-gliceropshospate and protease inhibitors (5 µg/ml 4-(2-aminoethyl)bencenesulfonyl fluoride, 5 µg (ml leupeptin, 5 µg/ml aprotinin and 1 µg/ml pepstatin A). The lysates were centrifuged at 14,000×g (4° C., 10 min) and then incubated with Glutation-Agarose Beads (GAB, Amersham Pharmacia) previously fitted with GST-Pak at 4° C. for 1 hour. After washing, the GABs were boiled for 5 minutes in loading buffer. The samples were separated in a 12% SDS-polyacrilamide gel and electrotrasferred to a PVDF membrane for its ulterior "Western Blot" analysis using an anti-Rac1 antibody (Sigma). The total Rac levels were analyzed in a similar way from aliquots taken from the cell lysate.

Figure 3:
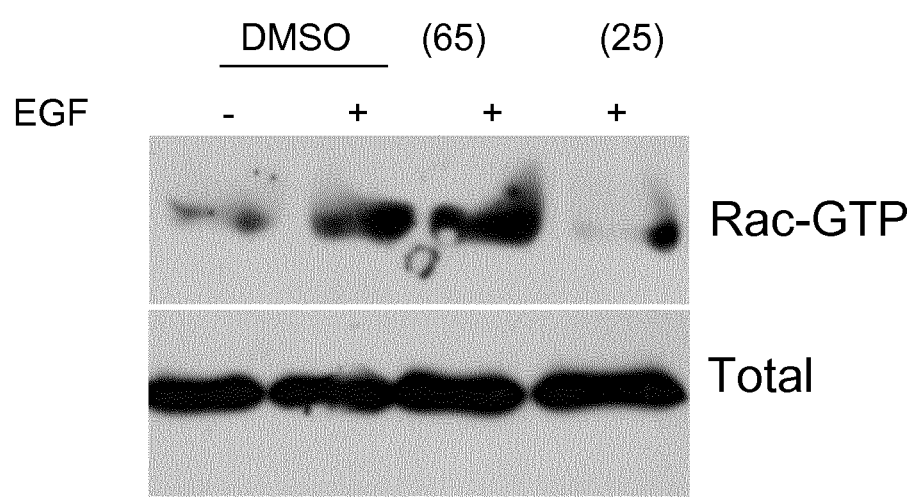
FIG. 3: Pull down assay of compounds (65) and (25) with LN229 human glioblastoma cells. Western Blot shows levels of intracellular Rac activation at 10 µM.

FIG. 3 shows the inhibitory effect of compounds (25) and (65) over the intracellular active Rac levels at 10 µM.

Figure 4:
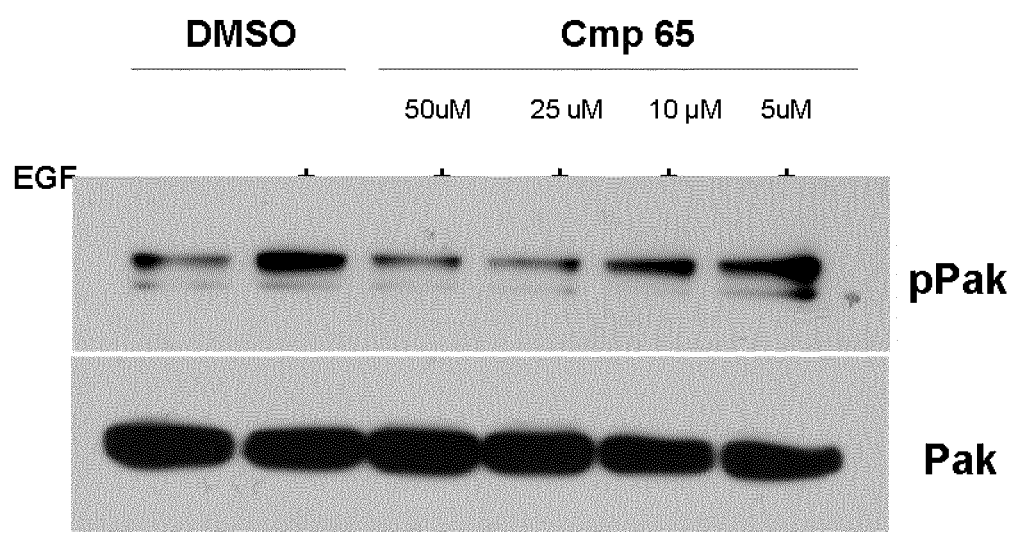
FIG. 4: Phosphorilation leves of PAK after treatment with compound (65) at different doses.

Following, the effect of compound (65) over the PAK1 activation was evaluated. Starvated cells for 48 hours were treated with compound (65) for 1 hour and they were actived with EGF 100 ng/ml. FIG. 4 shows the decrease of PAK phosphorilation with the increase of compound (65) concentration.

Figure 5:
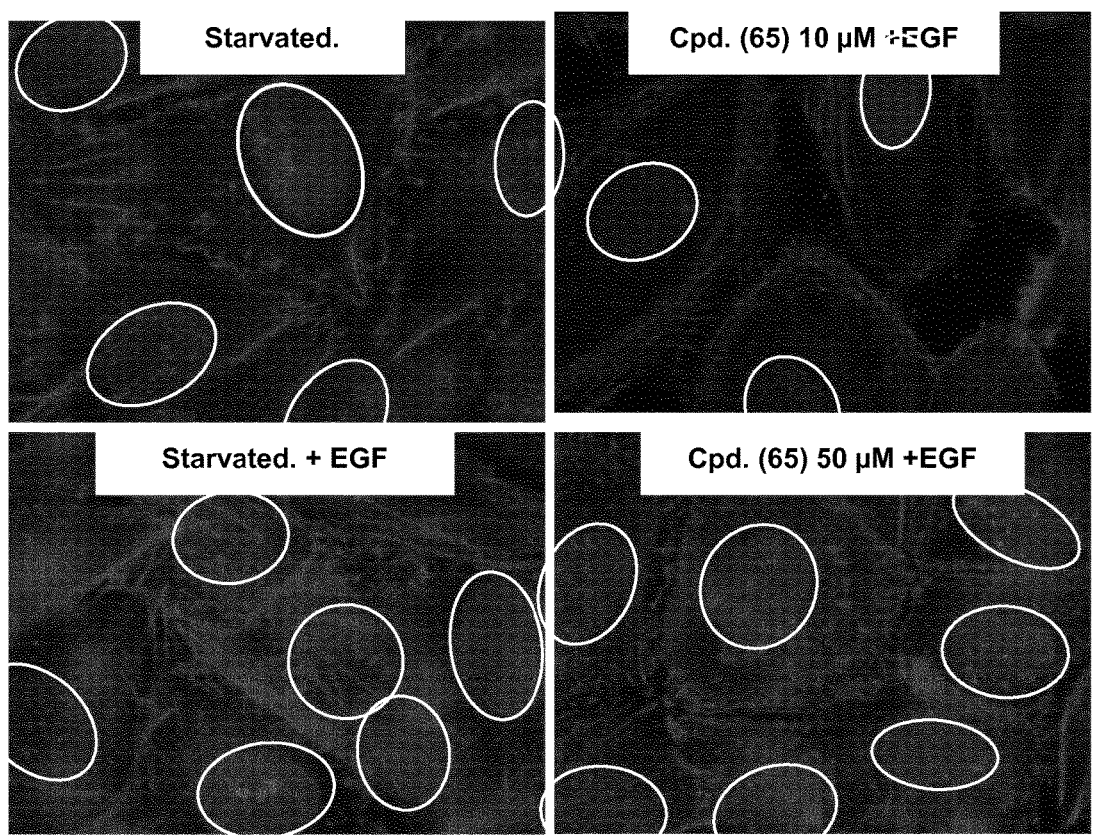
FIG. 5: Actin cytoskeleton reorganization over LN229 human glioblastoma cells.

The effect of compound (65) over the polymerization of actin filaments was evaluated by immunofluorescence with conjugated faloidine with the fluorochrome AlexaFluor (Invitrogen). LN229 human glioblastoma cells were starvated for 24 hours, treated with compound (65) for 1 hour, and stimulated with EGF. As expected, EGF induced the polymerization of actin filaments in no-treated cells, whereas cells treated with compound (65) shown a decreasing of intracellular fibrilar actin levels and a diffuse sign in the cellular citoplasm (c.f. FIG. 5). An accurate sign of cellular boundaries is observed in all cells due to the cortical actin marking.

Example 4

Antimigration Effect

Cell motility is a key process in the invasion and tumor metastasis processes and it is closely regulated by the Rho-GTPases family, particularly by Rac. This assay consists in the determination of the antimigration effect of compound (65) on LN229 human glioblastoma cells.

The cell migration in vitro was measured by the trans-well migration assay, wherein LN229 cells previously treated with different concentrations (10 µM, 50 µM and 100 µM) of compound (65) and serum deprived were placed on the upper layer of a cell permeable membrane of a trans-well plaque. Following an incubation perior of 24 hours, the cells migrated through the 8 µm pores of the membrane to the lower layer.

Figure 6:
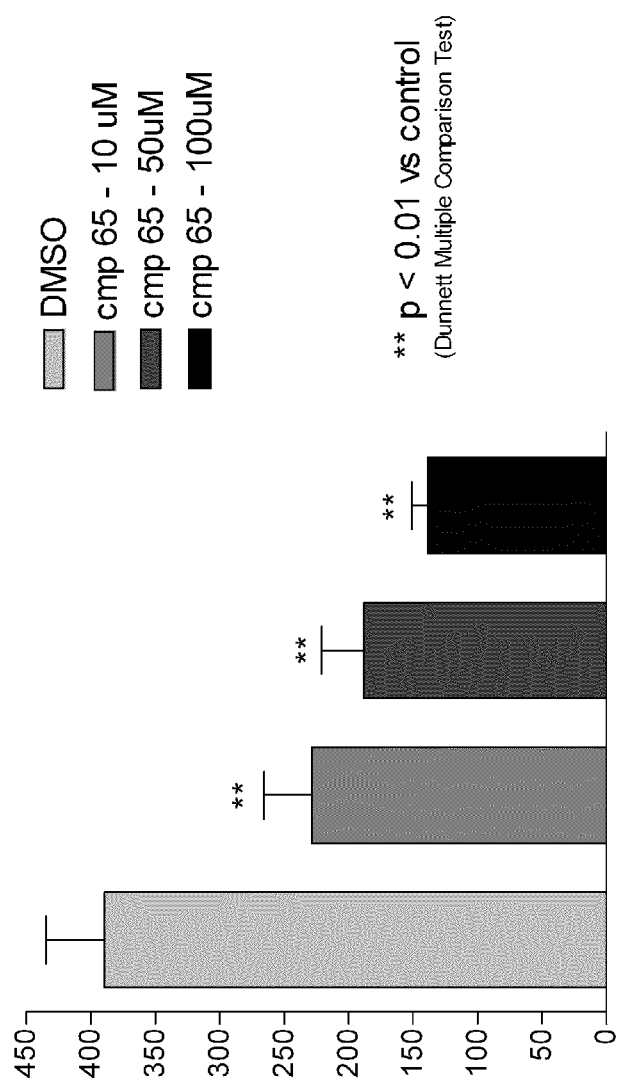
FIG. 6: Trans-well migration assay with LN229 human glioblastoma cells.

FIG. 6 shows that all the treatments significantly decreased the cell migration in a dose dependent manner

Example 5

Cell Cycle Effect

The effect of compound (65) on the cell cycle was studied by flow citometry. It is known that Rac1 GTPase is related with transcription of molecules such as cyclin D1, which are required to progress from G1 phase to S phase. Inhibition of Rac1 induces cell arrest in G0-G1 phase.

Figure 7:
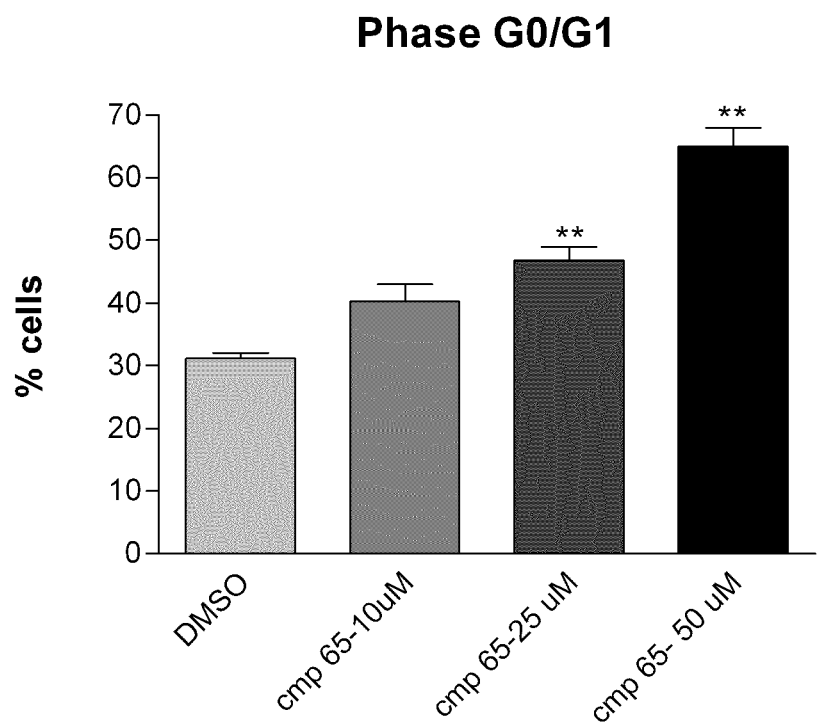
FIG. 7: The effect of compound (65) on the cell cycle of LN229 human glioblastoma cells. **p<0.001 ANOVA cont. Dunnett's Multiple Comparison Test

LN229 cells synchronized in G0-G1 phase and stimulated for 24 hours with FBS were treated with compound (65). FIG. 7 shows that in presence of 50 µM of compound (65), 60% of cell population is in G0-G1 phase, whereas controls shows only 25% of cell population in this phase. Therefore, it is shown that compound (65) arrests tumoral cells in G0-G1 phase in a dose dependent manner.

Example 6

Antiproliferative Assay

Figure 8:
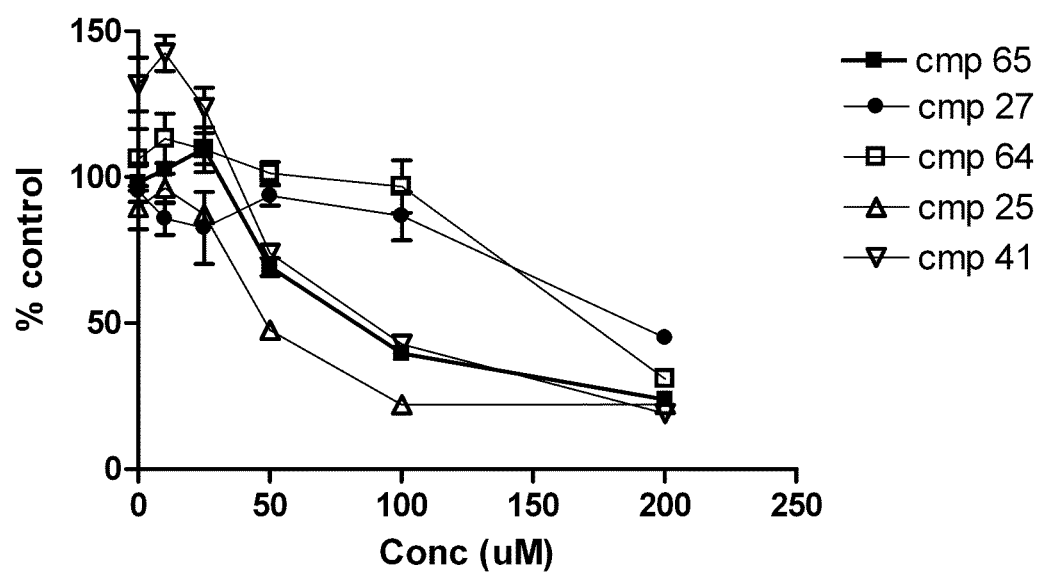
FIG. 8: Antiproliferative effect of compounds (65), (25), (27), (41) and (64) over LN229 human glioblastoma cells.

The antiproliferative effect of compounds (65), (25), (27), (41) and (64) was tested over LN229 human glioblastoma cells (c.f FIG. 8).

Cells were maintained in monolayer culture with the corresponding media, supplemented with 5% fetal bovine serum (FBS) previously inactivated with heat, 2 mM glutamine and 80 mg/ml gentamicine.

The cells were trated for 72 hours in the presence of FBS 10% with different doses of the compounds in 96 wells at a 2500 cell/well density. The cell growth was estimated by MTT test, for which to the cell monolayers was added MTT, incubated and resuspended in DMSO. Finally, the number of cells was estimated by measuring the absorbance values at 570 nm.

Example 7

Antimetastatic Effect of (25) on F3II Mammary Carcinoma Cells

Specific pathogen-free female BALB/c inbred mice from UNLP (Buenos Aires, Argentina), with an age of 8-10 weeks and a average weight of 20 g, were used. They were housed in plastic cages under standard conditions and had access to rodent chow and water ad libitum. On the designated day 0 of the experiment, F3II mammary carcinoma cells were injected into the lateral tail vein of unanesthetized mice at a concentration of $2 \times 10^5$ viable cells/0.3 ml DMEM/mice. At day 21, animals were sacrificed by cervical dislocation and necropsied. To investigate the presence of lung metastasis, lungs were removed, fixed in Bouin's solution and the number of surface nodules was determined under a dissecting microscope.

Figure 9:
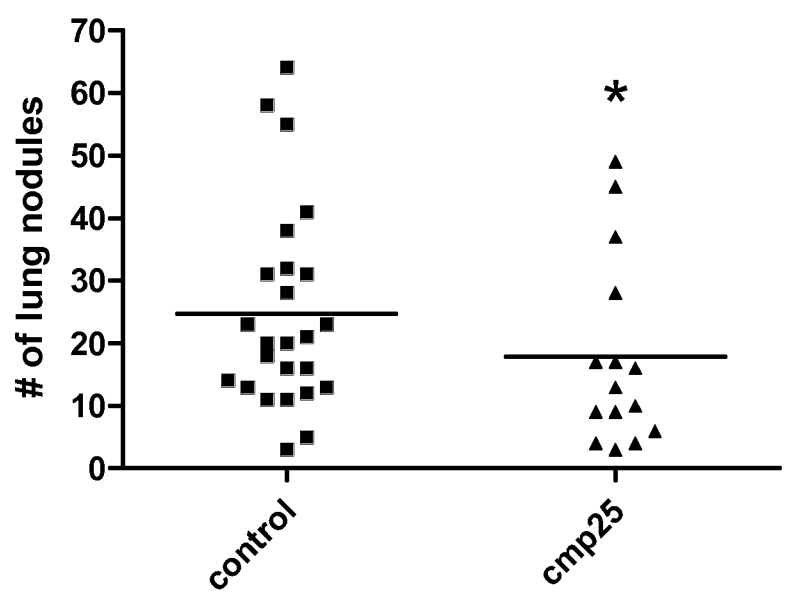
FIG. 9: Antimetastatic effect of compound (25) on F3II cells. Results from three independent experiments are presented together. *P<0.05 Mann-Whitney test.

To study the effect of compound (25) on metastatic lung colonization, mice were injected i.p at daily doses of 25 mg/kg body weight from days 0 to 21. The results are presented in FIG. 9. Daily treatment of mice with compound (25) at (25 mg/kg/day) significantly reduced by about 35% the formation of metastatic lung colonies.

As expected, compound (25) was well tolerated in adult female BALB/c mice. In all cases, treatment caused no significant changes in animal weight when compared to the control group.

The invention claimed is:

1. A method for treating a cancer mediated by Rho-GTPase cell proteins in a human which comprises administering to said human an effective amount of a compound of formula (I):

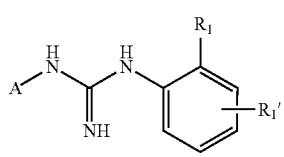

(I)

or a salt thereof, or any of its stereoisomeric forms or a mixture thereof wherein:

$R_1$ is $CF_3$ and $R_1'$ is H;

wherein A is selected from:

A is a radical selected from linear or branched (C1-C6) alkyl or one of the known carbocyclic or heterocyclic ring systems with 1-2 rings, wherein each of the rings forming the ring system:

has 5-7 members, each member independently selected from C, N, O, S, CH, $CH_2$, NH; and is saturated, partially unsaturated or aromatic;

wherein A is substituted by one or more radicals selected from the group consisting of H, halogen, nitro, cyano, linear or branched ($C_1$-$C_6$)alkyl, halo-($C_1$-$C_6$)alkyl, linear or branched ($C_2$-$C_6$)alkenyl, —$OR_2$, —$COR_2$, —$COOR_2$, —$OC(O)R_2$, —C(O)$NR_3R_4$, —$NR_3R_4$, —$R_5NHR_6$, —$SR_2$, —SO—$R_2$, —$SO_2$—$R_2$, and —$SO_2NR_3R_4$;

wherein each $R_2$ independently represents H or linear or branched ($C_1$-$C_4$)alkyl, each $R_3$ independently represents H or linear or branched ($C_1$-$C_4$)alkyl, each $R_4$ independently represents H, linear or branched ($C_1$-$C_6$)alkyl, phenyl, pyridine or quinoline; wherein the phenyl, pyridine and quinoline ring system is substituted by one or more radical selected from H, linear or branched ($C_1$-$C_4$)alkyl, and $NH_2$;

$R_5$ and $R_6$ are independently selected from H, linear or branched ($C_1$-$C_4$)alkyl, together with pharmaceutical excipients or carriers.

2. The method according to claim 1, wherein A is a ring system selected from

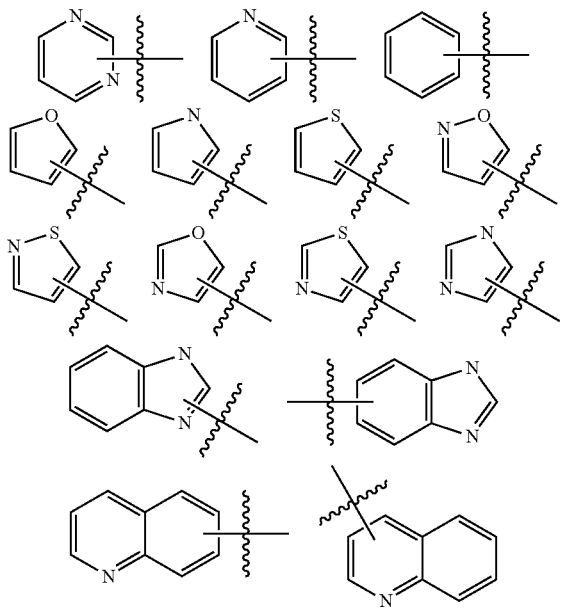

wherein the wavy line indicates the point of attachment of the ring to the adjacent nitrogen, and wherein A is substituted as defined in claim 1.

3. The method according to claim 2, wherein A is a ring system selected from

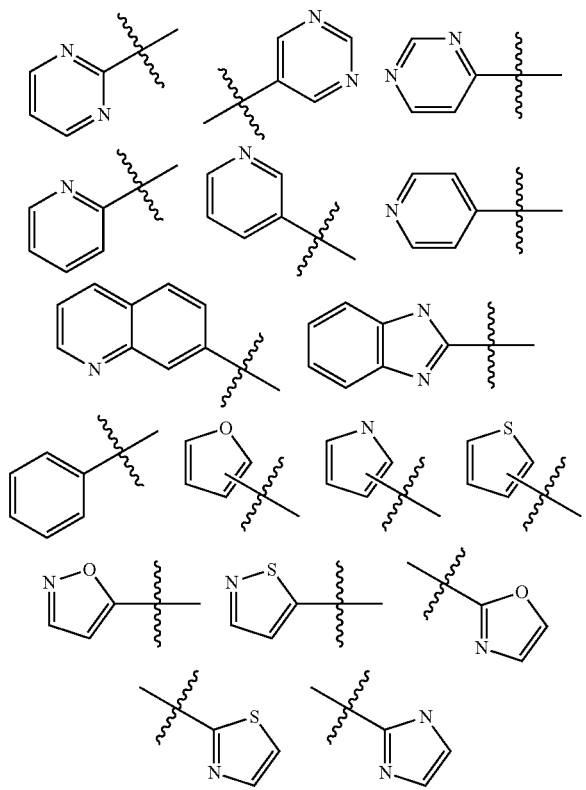

wherein the wavy line indicates the point of attachment of the ring to the adjacent nitrogen; and wherein A is substituted by one or more radicals as defined in claim 1.

4. The method according to claim 3, wherein the ring system of A is substituted by one or more radicals selected from the group consisting of H, F, Cl, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$CH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2$N($CH_3$)$_2$, —$SO_2$N($CH_2CH_3$)$_2$, —$SO_2$N($CH_2CH_2CH_3$)$_2$, —$SO_2$N($CH_2CH_2CH_2CH_3$)$_2$ and —$SO_2$N($CH_2CH(CH_3)_2$)$_2$.

5. The method according to claim 1, wherein the compound is of formula Ia:

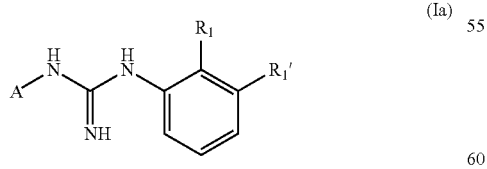

(Ia)

or a salt thereof, or any of its stereoisomeric forms or a mixture thereof;
wherein $R_1$ is $CF_3$ and $R_1'$ is H.

6. The method according to claim 5, wherein A is a radical of one of the known heterocyclic ring systems with 1-2 rings, wherein each of the rings forming the ring system
has 5-7 members, each member independently selected from C, N, O, S, CH, $CH_2$, NH;
is saturated, partially unsaturated or aromatic;
wherein A is substituted by one or more radical selected from the group consisting of H, F, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$COCH_3$, —COOH, —$COOCH_3$, —$COOCH_2CH_3$, —OC(O)H, —OC(O)$CH_3$, —C(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2$N($CH_3$)$_2$, —$SO_2$N($CH_2CH_3$)$_2$, —$SO_2$N($CH_2CH_2CH_3$)$_2$, —$SO_2$N($CH_2CH_2CH_2CH_3$)$_2$ and —$SO_2$N($CH_2CH(CH_3)_2$)$_2$.

7. The method according to claim 5, wherein A is a phenyl radical substituted by one or more radicals selected from the group consisting of H, F, Cl, Br, I, nitro, cyano, methyl, ethyl, n-propyl, i-propyl, n-butyl, t-butyl, —$CF_3$, —$CH_2CF_3$, linear or branched ($C_2$-$C_6$)alkenyl, —OH, —$OCH_3$, —$OCH_2CH_3$, —COH, —$OCH_3$, —COOH, —$COOCH_3$, —$COOCH_2CH_3$, —OC(O)H, —OC(O)$CH_3$, —(O)$NH_2$, —$NH_2$, —$NHCH_3$, —N($CH_3$)$_2$, —$CH_2NH_2$, —$CH_2NHCH_3$, —$SH_2$, —SO—$CH_3$, —$SO_2$—$CH_3$, —$SO_2NH_2$, —$SO_2NHCH_3$, —$SO_2NHCH_2CH_3$, —$SO_2$N($CH_3$)$_2$, —$SO_2$N($CH_2CH_3$)$_2$, —$SO_2$N($CH_2CH_2CH_3$)$_2$, —$SO_2$N($CH_2CH_2CH_2CH_3$)$_2$ and —$SO_2$N($CH_2CH(CH_3)_2$)$_2$.

8. The method according to claim 1, wherein the compound is selected from:
N-pyrimidin-2-yl-N'-[2-(trifluoromethyl)phenyl]guanidine (1);
N-(4-ethyl-6-methylpyrimidin-2-yl)-N'-[2-(trifluoromethyl)phenyl]guanidine (2);
N-(4-methyl-6-propylpyrimidin-2-yl)-N'-[2-(trifluoromethyl)phenyl]guanidine (3);
N-(4-isopropyl-6-methylpyrimidin-2-yl)-N'-[2-(trifluoromethyl)phenyl]guanidine (4);
N-(4-butyl-6-methylpyrimidin-2-yl)-N'-[2-(trifluoromethyl)phenyl]guanidine (5);
N-(4-tert-butyl-6-methylpyrimidin-2-yl)-N'-[2-(trifluoromethyl)phenyl]guanidine (6);
N-(4,6-diaminopyrimidin-2-yl)-N'-[2-(trifluoromethyl)phenyl]guanidine (7);
N-(4,6-dichloropyrimidin-2-yl)-N'-[2-(trifluoromethyl)phenyl]guanidine (8);
N-(4,6-difluoropyrimidin-2-yl)-N'-[2-(trifluoromethyl)phenyl]guanidine (9);
N-[4-methyl-6-(trifluoromethyl)pyrimidin-2-yl]-N'-[2-(trifluoromethyl)phenyl]guanidine (10);
N-(4-cyano-6-methylpyrimidin-2-yl)-N'-[2-(trifluoromethyl)phenyl]guanidine (11);
N-(5-methylpyrimidin-2-yl)-N'-[2-(trifluoromethyl)phenyl]guanidine (12);
N-(4-chloro-6-methylpyrimidin-2-yl)-N'-[2-(trifluoromethyl)phenyl]guanidine (13);
N-(4-fluoro-6-methylpyrimidin-2-yl)-N'-[2-(trifluoromethyl)phenyl]guanidine (14);
N-(4-fluoropyrimidin-2-yl)-N'-[2-(trifluoromethyl)phenyl]guanidine (15);
N-(5-fluoropyrimidin-2-yl)-N'-[2-(trifluoromethyl)phenyl]guanidine (16);
N-[4,6-bis(trifluoromethyl)pyrimidin-2-yl]-N'-[2-(trifluoromethyl)phenyl]guanidine (17);

N-(4,6-dicyanopyrimidin-2-yl)-N'-[2-(trifluoromethyl)
  phenyl]guanidine (18);
N-pyridin-2-yl-N'-[2-(trifluoromethyl)phenyl]guanidine
  (19);
N-pyridin-3-yl-N'-[2-(trifluoromethyl)phenyl]guanidine
  (20);
N-pyridin-4-yl-N'-[2-(trifluoromethyl)phenyl]guanidine
  (21);
N-pyrimidin-4-yl-N'-[2-(trifluoromethyl)phenyl]guanidine (22);
N-pyrimidin-5-yl-N-[2-(trifluoromethyl)phenyl]guanidine (23);
N-(4,6-dimethylpyridin-2-yl)-N'-[2-(trifluoromethyl)phenyl]guanidine (24);
N-(3,5-dimethylphenyl)-N-[2-(trifluoromethyl)phenyl] guanidine (25);
N-(2,6-dimethylpyridin-4-yl)-N'-[2-(trifluoromethyl)phenyl]guanidine (26);
N-phenyl-N'-[2-(trifluoromethyl)phenyl]guanidine (27);
2-[(imino{[2-(trifluoromethyl)phenyl]amino}methyl)
  amino]-N,N-dimethylbenzenesulfonamide (28);
2-[(imino{[2-(trifluoromethyl)phenyl]amino}methyl)
  amino]-N,N-diethylbenzenesulfonamide (29);
2-[(imino{[2-(trifluoromethyl)phenyl]amino}methyl)
  amino]-N,N-dipropylbenzenesulfonamide (30);
2-[(imino{[2-(trifluoromethyl)phenyl]amino}methyl)
  amino]-N,N-dibutylbenzenesulfonamide (31);
3-[(imino{[2-(trifluoromethyl)phenyl]amino}methyl)
  amino]-N,N-dimethylbenzenesulfonamide (32);
3-[(imino{[2-(trifluoromethyl)phenyl]amino}methyl)
  amino]-N,N-diethylbenzenesulfonamide (33);
3-[(imino{[2-(trifluoromethyl)phenyl]amino}methyl)
  amino]-N,N-dipropylbenzenesulfonamide (34);
3-[(imino{[2-(trifluoromethyl)phenyl]amino}methyl)
  amino]-N,N-dibutylbenzenesulfonamide (35);
4-[(imino{[2-(trifluoromethyl)phenyl]amino}methyl)
  amino]-N,N-dimethylbenzenesulfonamide (36);
4-[(imino{[2-(trifluoromethyl)phenyl]amino}methyl)
  amino]-N,N-diethylbenzenesulfonamide (37);
4-[(imino{[2-(trifluoromethyl)phenyl]amino}methyl)
  amino]-N,N-dipropylbenzenesulfonamide (38);
4-[(imino{[2-(trifluoromethyl)phenyl]amino}methyl)
  amino]-N,N-dibuthylbenzenesulfonamide (39);
N-(2-nitrophenyl)-N'-[2-(trifluoromethyl)phenyl]guanidine (40);
N-(3-nitrophenyl)-N'-[2-(trifluoromethyl)phenyl]guanidine (41);
N-(4-nitrophenyl)-N'-[2-(trifluoromethyl)phenyl]guanidine (42);
N-2-thienyl-N'-[2-(trifluoromethyl)phenyl]guanidine (43);
N-3-thienyl-N'-[2-(trifluoromethyl)phenyl]guanidine (44);
N-1H-pyrrol-2-yl-N'-[2-(trifluoromethyl)phenyl]guanidine (45);
N-1H-pyrrol-3-yl-N'-[2-(trifluoromethyl)phenyl]guanidine (46);
N-2-furyl-N'-[2-(trifluoromethyl)phenyl]guanidine (47);
N-3-furyl-N'-[2-(trifluoromethyl)phenyl]guanidine (48);
N-1,3-oxazol-2-yl-N'-[2-(trifluoromethyl)phenyl]guanidine (49);
N-1,3-thiazol-2-yl-N'-[2-(trifluoromethyl)phenyl]guanidine (50);
N-1H-imidazol-2-yl-N'-[2-(trifluoromethyl)phenyl] guanidine (51);
N-isoxazol-5-yl-N'-[2-(trifluoromethyl)phenyl]guanidine (52);
N-1H-benzimidazol-2-yl-N'-[2-(trifluoromethyl)phenyl] guanidine (53);
N-(3,4-dimethylisoxazol-5-yl)-N'-[2-(trifluoromethyl) phenyl]guanidine (54);
1-(4-(4-amino-2-methylquinolin-7-ylamino)pyrimidin-2-yl)-3-(2-(trifluoromethyl)phenyl)guanidine (57);
N-(4-amino-2-methylquinolin-7-yl)-N'-[2-(trifluoromethyl)phenyl]guanidine (58);
N-quinolin-7-yl-N'-[2-(trifluoromethyl)phenyl]guanidine (59);
N-methyl-N'-[2-(trifluoromethyl)phenyl]guanidine (60);
N-ethyl-N'-[2-(trifluoromethyl)phenyl]guanidine (61);
N-propyl-N'-[2-(trifluoromethyl)phenyl]guanidine (62);
N-buthyl-N'-[2-(trifluoromethyl)phenyl]guanidine (63);
N-(2-methylphenyl)-N'-[2-(trifluoromethyl)phenyl] guanidine (64); and
N-[4,6-bis(methyl)pyrimidin-2-yl]-N'-[2-(trifluoromethyl)phenyl]guanidine (65).

9. The method according to claim 1, wherein the compound is selected from:
N-[4,6-bis(methyl)pyrimidin-2-yl]-N'-[2-(trifluoromethyl)phenyl]guanidine (65),
N-(3,5-dimethylphenyl)-N'-[2-(trifluoromethyl)phenyl] guanidine (25),
N-phenyl-N'-[2-(trifluoromethyl)phenyl]guanidine (27),
N-(3-nitrophenyl)-N'-[2-(trifluoromethyl)phenyl]guanidine (41),
N-[4-methyl-6-(trifluoromethyl)pyrimidin-2-yl]-N'-[2-(trifluoromethyl)phenyl]guanidine (10), and
N-(2-methylphenyl)-N'-[2-(trifluoromethyl)phenyl] guanidine (64).

10. The method according to claim 1, wherein the cancer mediated by Rho-GTPase cell proteins is a proliferative disorder selected from the group consisting of precancerosis; dysplasia; metaplasia; carcinomas of the gastrointestinal or colorectal tract, liver, pancreas, kidney, bladder, prostate, endometrium, ovary, testes, melanoma, dysplastic oral mucosa, invasive oral cancers, small cell and non-small cell lung carcinomas, hormone-dependent breast cancers, hormone-independent breast cancers, transitional and squamous cell cancers, neurological malignancies including neuroblastoma, gliomas, glioblastoma, astrocytomas, osteosarcomas, soft tissue sarcomas, hemangioamas, endocrinological tumors, hematologic neoplasias including leukemias, lymphomas, and other myeloproliferative and lymphoproliferative diseases, carcinomas in situ, hyperplastic lesions, adenomas, fibromas, histiocytosis, chronic inflammatory proliferative diseases, vascular proliferative diseases, virus-induced proliferative diseases, and skin diseases characterized by hyperproliferation of keratinocytes and/or T cells.

11. The method according to any claim 1, wherein the method comprises administering to a subject simultaneously, sequentially or separately a compound of formula I and
i) one or more anticancer agents;
ii) radiotherapy;
iii) conventional surgery;
iv) or mixtures thereof.

12. A compound of formula (II)

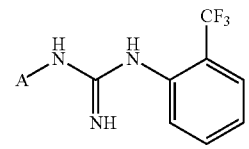

(II)

or a salt thereof, or any of its stereoisomeric forms or a mixture thereof wherein:

A is a radical of one of the known carbocyclic or heterocyclic ring systems with 1-2 rings, wherein each of the rings forming the ring system
has 5-7 members, each member independently selected from C, N, O, S, CH, CH$_2$, NH;
is saturated, partially unsaturated or aromatic;

wherein A is substituted by one or more radicals selected from the group consisting of H, F, Cl, Br, I, nitro, cyano, methyl, ethyl, n-propyl, i-propyl, n-butyl, t-butyl, linear or branched (C$_2$-C$_6$)alkenyl, —OH, —OCH$_3$, —OCH$_2$CH$_3$, —COH, —COCH$_3$, —COOH, —COOCH$_3$, —COOCH$_2$CH$_3$, —OC(O)H, —OC(O)CH$_3$, —C(O)NH$_2$, —NH$_2$, —NHCH$_3$, —N(CH$_3$)$_2$, —CH$_2$NH$_2$, —CH$_2$NHCH$_3$, —SH$_2$, —SO—CH$_3$, —SO$_2$—CH$_3$, —SO$_2$NH$_2$, —SO$_2$NHCH$_3$, —SO$_2$NHCH$_2$CH$_3$, —SO$_2$N(CH$_3$)$_2$, —SO$_2$N(CH$_2$CH$_3$)$_2$, —SO$_2$N(CH$_2$CH$_2$CH$_3$)$_2$, —SO$_2$N(CH$_2$CH$_2$CH$_2$CH$_3$)$_2$ and —SO$_2$N(CH$_2$CH(CH$_3$)$_2$)$_2$;

with the proviso that the compound is other than N-(4-methyl-6-hydroxy-pyrimidin-2-yl)-N'-(2-trifluoromethylphenyl)guanidine, N-[4,6-bis(methyl)pyrimidin-2-yl]-N'-[2-(trifluoromethyl)phenyl]guanidine or N-[(4-methyl)pyrimidin-2-yl]-N'-[2-(trifluoromethyl)phenyl]guanidine.

13. The compound according to claim 12, wherein A is a phenyl radical substituted by one or more radicals selected from the group consisting of H, F, Cl, Br, I, nitro, cyano, methyl, ethyl, n-propyl, i-propyl, n-butyl, t-butyl, linear or branched (C$_2$-C$_6$)alkenyl, —OH, —OCH$_3$, —OCH$_2$CH$_3$, —COH, —COCH$_3$, —COOH, —COOCH$_3$, —COOCH$_2$CH$_3$, —OC(O)H, —OC(O)CH$_3$, —C(O)NH$_2$, —NH$_2$, —NHCH$_3$, —N(CH$_3$)$_2$, —CH$_2$NH$_2$, —CH$_2$NHCH$_3$, —SH$_2$, —SO—CH$_3$, —SO$_2$—CH$_3$, —SO$_2$NH$_2$, —SO$_2$NHCH$_3$, —SO$_2$NHCH$_2$CH$_3$, —SO$_2$N(CH$_3$)$_2$, —SO$_2$N(CH$_2$CH$_3$)$_2$, —SO$_2$N(CH$_2$CH$_2$CH$_3$)$_2$, —SO$_2$N(CH$_2$CH$_2$CH$_2$CH$_3$)$_2$ and —SO$_2$N(CH$_2$CH(CH$_3$)$_2$)$_2$.

14. The compound according to claim 12, wherein A is a heterocyclic ring systems with 1-2 rings, wherein each of the rings forming the ring system
has 5-7 members, each member independently selected from C, N, O, S, CH, CH$_2$, NH;
is saturated, partially unsaturated or aromatic;

wherein A is substituted by one or more radicals selected from the group consisting of H, F, Cl, Br, I, nitro, cyano, methyl, ethyl, n-propyl, i-propyl, n-butyl, t-butyl, linear or branched (C$_2$-C$_6$)alkenyl, —OH, —OCH$_3$, —OCH$_2$CH$_3$, —COH, —COCH$_3$, —COOH, —COOCH$_3$, —COOCH$_2$CH$_3$, —OC(O)H, —OC(O)CH$_3$, —C(O)NH$_2$, —NH$_2$, —NHCH$_3$, —N(CH$_3$)$_2$, —CH$_2$NH$_2$, —CH$_2$NHCH$_3$, —SH$_2$, —SO—CH$_3$, —SO$_2$—CH$_3$, —SO$_2$NH$_2$, —SO$_2$NHCH$_3$, —SO$_2$NHCH$_2$CH$_3$, —SO$_2$N(CH$_3$)$_2$, —SO$_2$N(CH$_2$CH$_3$)$_2$, —SO$_2$N(CH$_2$CH$_2$CH$_3$)$_2$, —SO$_2$N(CH$_2$CH$_2$CH$_2$CH$_3$)$_2$ and —SO$_2$N(CH$_2$CH(CH$_3$)$_2$)$_2$;

with the proviso that the compound is other than N-(4-methyl-6-hydroxy-pyrimidin-2-yl)-N'-(2-trifluoromethylphenyl)guanidine, N-[4,6-bis(methyl)pyrimidin-2-yl]-N'-[2-(trifluoromethyl)phenyl]guanidine or N-[(4-methyl)pyrimidin-2-yl]-N'-[2-(trifluoromethyl)phenyl]guanidine.

15. A pharmaceutical composition comprising at least one compound of claim 12 and one or more pharmaceutically acceptable excipients or carriers.

16. The pharmaceutical composition according to claim 15, which further comprises another therapeutically active substance.

17. A process for preparing the compound of claim 1, which comprises reacting a compound of formula (III) with a compound of formula (IV):

A—NH$_2$·HCl  (III)

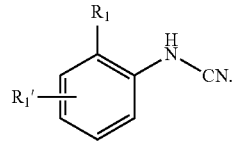

(IV)

* * * * *